United States Patent
Bostian et al.

(10) Patent No.: US 7,462,153 B2
(45) Date of Patent: Dec. 9, 2008

(54) METHOD AND SYSTEM FOR MODELING CARDIOVASCULAR DISEASE USING A PROBABILITY REGESSION MODEL

(75) Inventors: Aj A. Bostian, Charlottesville, VA (US); Sailor H. Mohler, Columbia, MD (US); Sidney E. Bostian, Jr., Fairfax, VA (US)

(73) Assignee: Sonomedica, Inc., Vienna, VA (US)

( * ) Notice: Subject to any disclaimer, the term of this patent is extended or adjusted under 35 U.S.C. 154(b) by 659 days.

(21) Appl. No.: 10/897,121

(22) Filed: Jul. 23, 2004

(65) Prior Publication Data

US 2006/0020220 A1 Jan. 26, 2006

(51) Int. Cl.
*A61B 5/02* (2006.01)
(52) U.S. Cl. ...................... 600/508; 600/528
(58) Field of Classification Search ................. 600/508, 600/513, 514, 528
See application file for complete search history.

(56) References Cited

U.S. PATENT DOCUMENTS 6,024,705 A * 2/2000 Schlager et al. ............. 600/508

OTHER PUBLICATIONS

Munt et al. "Physical examination in valvularaortic stenosis: Correlation with stenosis severity and prediction of clinical outcome", American Heart Journal, vol. 13, No. 2, Feb. 1999, pp. 298-306.*

* cited by examiner

*Primary Examiner*—Carl H. Layno
*Assistant Examiner*—Brian T Gedeon
(74) *Attorney, Agent, or Firm*—Hanify & King, P.C.

(57) ABSTRACT

A method and system for modeling cardiovascular disease using a probability regression model is provided. A parameter estimate of a probability regression model for cardiovascular disease can be generated using predictors derived from cardiovascular sound signals and disease status information. A probability of cardiovascular disease can be generated using a probability regression model that includes a predictor derived from cardiovascular sound signals.

53 Claims, 20 Drawing Sheets

DATASET A

Disease Status Information

| (1) ID | (2) RCA | (3) LAD | (4) LCX | (5) BP_SYST | (6) BP_DIAS |
|---|---|---|---|---|---|
| 1 | 5 | 5 | 5 | 130 | 59 |
| 2 | 29 | 57 | 33 | 167 | 80 |
| 3 | 8 | 15 | 13 | 102 | 57 |
| 4 | 12 | 25 | 12 | 152 | 71 |
| 5 | 44 | 27 | 14 | 133 | 56 |
| 6 | 75 | 55 | 85 | 114 | 62 |
| 7 | 55 | 37 | 35 | 137 | 75 |
| 8 | 32 | 16 | 36 | 99 | 73 |
| 9 | 100 | 62 | 35 | 121 | 38 |
| 10 | 38 | 28 | 54 | 159 | 84 |
| 11 | 26 | 15 | 20 | 190 | 81 |
| 12 | 24 | 18 | 18 | 130 | 78 |
| 13 | 26 | 26 | 33 | 133 | 71 |
| 14 | 15 | 23 | 35 | 174 | 99 |
| 15 | 43 | 32 | 46 | 141 | 78 |
| 16 | 5 | 24 | 15 | 134 | 77 |
| 17 | 25 | 15 | 18 | 119 | 63 |
| 18 | 49 | 81 | 65 | 105 | 63 |
| 19 | 100 | 60 | 30 | 162 | 92 |
| 20 | 41 | 100 | 32 | 142 | 72 |
| 21 | 14 | 28 | 16 | 154 | 77 |
| 22 | 5 | 21 | 21 | 137 | 73 |
| 23 | 17 | 22 | 14 | 125 | 56 |
| 24 | 5 | 15 | 10 | 136 | 73 |
| 25 | 8 | 9 | 5 | 141 | 94 |
| 26 | 19 | 34 | 6 | 132 | 62 |
| 27 | 15 | 16 | 16 | 131 | 70 |
| 28 | 11 | 9 | 16 | 121 | 79 |
| 29 | 70 | 35 | 65 | 153 | 78 |
| 30 | 41 | 58 | 48 | 114 | 74 |
| 31 | 0 | 63 | 27 | 160 | 70 |
| 32 | 80 | 55 | 20 | 136 | 91 |
| 33 | 17 | 12 | 20 | 167 | 95 |
| 34 | 55 | 50 | 20 | 144 | 82 |
| 35 | 10 | 19 | 0 | 141 | 66 |
| 36 | 15 | 16 | 28 | 108 | 66 |
| 37 | 100 | 30 | 15 | 115 | 62 |
| 38 | 8 | 47 | 22 | 151 | 88 |
| 39 | 100 | 67 | 100 | 160 | 63 |
| 40 | 16 | 10 | 17 | 120 | 79 |

Fig. 6

DATASET A

Data Derived from Cardiovascular Sound Signals

| (1) ID | (7) BEATS_R | (8) BEATS_C | (9) BEATS_L | (10) FMS_R | (11) FMS_C | (12) FMS_L | (13) S3_R | (14) S3_C | (15) S3_L |
|---|---|---|---|---|---|---|---|---|---|
| 1 | 37 | 35 | 48 | 0 | 0 | 0.017 | 10 | 2 | 27 |
| 2 | 24 | 24 | 25 | 0.107 | 0 | 0.146 | 3 | 3 | 3 |
| 3 | 26 | 23 | 22 | 0.013 | 0.021 | 0 | 14 | 16 | 11 |
| 4 | 36 | 37 | 37 | 0 | 0.011 | 0.051 | 6 | 20 | 13 |
| 5 | 28 | 7 | 29 | 0.133 | 0 | 0.092 | 10 | 5 | 12 |
| 6 | 26 | 25 | 27 | 0 | 0.043 | 0.082 | 21 | 2 | 0 |
| 7 | 27 | 26 | 31 | 0.154 | 0.08 | 0.372 | 18 | 6 | 23 |
| 8 | 24 | 23 | 22 | 0.247 | 0.101 | 0.332 | 13 | 14 | 15 |
| 9 | 22 | 21 | 21 | 0.036 | 0.035 | 0.156 | 19 | 18 | 15 |
| 10 | 38 | 38 | 38 | 0.132 | 0.235 | 0.018 | 19 | 0 | 13 |
| 11 | 43 | 43 | 43 | 0 | 0.022 | 0.091 | 18 | 3 | 0 |
| 12 | 28 | 29 | 34 | 0.307 | 0.156 | 0.188 | 0 | 14 | 10 |
| 13 | 26 | 24 | 26 | 0.064 | 0.12 | 0.029 | 7 | 23 | 2 |
| 14 | 33 | 33 | 33 | 0.01 | 0 | 0.283 | 16 | 32 | 0 |
| 15 | 20 | 25 | 21 | 0.161 | 0.055 | 0.131 | 7 | 22 | 5 |
| 16 | 32 | 37 | 30 | 0 | 0 | 0.027 | 22 | 22 | 0 |
| 17 | 34 | 35 | 38 | 0.028 | 0 | 0.012 | 4 | 6 | 13 |
| 18 | 31 | 33 | 32 | 0.2 | 0.25 | 0.059 | 20 | 14 | 0 |
| 19 | 28 | 29 | 29 | 0.002 | 0 | 0.122 | 19 | 21 | 9 |
| 20 | 31 | 32 | 32 | 0.184 | 0.268 | 0.085 | 15 | 32 | 25 |
| 21 | 22 | 22 | 22 | 0.049 | 0.043 | 0.05 | 22 | 13 | 17 |
| 22 | 36 | 37 | 37 | 0.181 | 0.034 | 0.082 | 25 | 21 | 22 |
| 23 | 38 | 37 | 38 | 0.055 | 0.07 | 0.022 | 29 | 20 | 31 |
| 24 | 34 | 34 | 33 | 0 | 0.124 | 0.249 | 5 | 14 | 23 |
| 25 | 27 | 28 | 27 | 0.003 | 0.02 | 0.017 | 14 | 4 | 15 |
| 26 | 33 | 31 | 34 | 0.174 | 0.029 | 0.51 | 4 | 0 | 0 |
| 27 | 27 | 30 | 32 | 0.038 | 0.113 | 0.294 | 2 | 9 | 1 |
| 28 | 30 | 30 | 30 | 0.114 | 0.077 | 0.02 | 22 | 11 | 25 |
| 29 | 27 | 24 | 25 | 0.045 | 0.153 | 0.084 | 7 | 1 | 1 |
| 30 | 28 | 29 | 28 | 0.238 | 0.061 | 0 | 24 | 25 | 15 |
| 31 | 46 | 46 | 47 | 0.094 | 0.11 | 0.116 | 18 | 7 | 18 |
| 32 | 23 | 23 | 24 | 0.02 | 0.009 | 0.115 | 15 | 12 | 2 |
| 33 | 37 | 35 | 38 | 0 | 0 | 0.056 | 7 | 5 | 2 |
| 34 | 32 | 27 | 27 | 0.177 | 0.018 | 0.085 | 17 | 18 | 13 |
| 35 | 21 | 20 | 21 | 0.048 | 0.015 | 0.078 | 16 | 13 | 1 |
| 36 | 30 | 30 | 34 | 0.047 | 0.132 | 0.111 | 11 | 5 | 5 |
| 37 | 32 | 29 | 28 | 0.083 | 0.069 | 0.304 | 22 | 15 | 17 |
| 38 | 30 | 31 | 31 | 0.042 | 0 | 0.194 | 16 | 14 | 3 |
| 39 | 43 | 42 | 43 | 0 | 0.089 | 0.075 | 10 | 29 | 32 |
| 40 | 35 | 29 | 39 | 0.093 | 0.037 | 0.06 | 2 | 11 | 12 |

Fig. 7

DATASET A

Data Derived from Cardiovascular Sound Signals

| (1) ID | (16) S4_R | (17) S4_C | (18) S4_L | (19) HR_R | (20) HR_C | (21) HR_L | (22) HRSD_R | (23) HRSD_C | (24) HRSD_L |
|---|---|---|---|---|---|---|---|---|---|
| 1 | 33 | 10 | 48 | 75.1 | 75.6 | 74.2 | 3 | 2.8 | 3.7 |
| 2 | 9 | 14 | 19 | 51.4 | 52 | 51.1 | 1 | 0.6 | 1.1 |
| 3 | 12 | 22 | 17 | 52.3 | 51.3 | 49.9 | 1.4 | 1.2 | 1.4 |
| 4 | 23 | 34 | 25 | 76 | 76 | 77.9 | 0.8 | 1.6 | 1.1 |
| 5 | 6 | 7 | 10 | 60.2 | 60 | 60.4 | 2 | 5 | 4.6 |
| 6 | 19 | 3 | 21 | 55.7 | 54.5 | 57.8 | 1.6 | 1.1 | 1.6 |
| 7 | 25 | 26 | 24 | 57.6 | 56.4 | 55.8 | 1.2 | 1.4 | 1.8 |
| 8 | 21 | 19 | 21 | 51.7 | 52.2 | 49.2 | 1.7 | 4.2 | 1.1 |
| 9 | 20 | 19 | 16 | 46.9 | 45.9 | 47.9 | 3.3 | 3.4 | 1.8 |
| 10 | 35 | 8 | 38 | 79.2 | 74 | 71.9 | 1.6 | 1.6 | 1.9 |
| 11 | 24 | 14 | 26 | 91.3 | 88.6 | 90.8 | 3.3 | 3.8 | 2.9 |
| 12 | 26 | 28 | 33 | 61.2 | 62.1 | 65.3 | 1.4 | 4.9 | 1.6 |
| 13 | 25 | 24 | 7 | 55.8 | 57.8 | 54 | 0.9 | 7.1 | 1.1 |
| 14 | 31 | 0 | 16 | 71.1 | 68.9 | 70.9 | 1.3 | 0.9 | 1.4 |
| 15 | 13 | 10 | 8 | 44.4 | 46.2 | 46.2 | 3.3 | 3.3 | 3.6 |
| 16 | 22 | 14 | 20 | 66.8 | 67 | 67.2 | 2.4 | 2.4 | 2.4 |
| 17 | 11 | 26 | 34 | 71.9 | 71.9 | 73.9 | 4.4 | 3.1 | 4.9 |
| 18 | 31 | 27 | 27 | 64.9 | 66 | 64.8 | 1.1 | 3.6 | 3.1 |
| 19 | 24 | 24 | 4 | 60.6 | 60.7 | 60.5 | 1.2 | 1.2 | 4.6 |
| 20 | 31 | 12 | 30 | 65.4 | 66.8 | 66.8 | 0.9 | 6.4 | 0.8 |
| 21 | 16 | 21 | 22 | 47.9 | 47.3 | 46.1 | 1.2 | 1.6 | 1 |
| 22 | 24 | 29 | 31 | 76 | 76.5 | 78 | 4.6 | 5.2 | 9.1 |
| 23 | 25 | 25 | 4 | 80.5 | 85.4 | 76.7 | 1.6 | 1.8 | 1 |
| 24 | 24 | 30 | 31 | 72.7 | 71.2 | 71.7 | 0.9 | 0.8 | 1.1 |
| 25 | 16 | 10 | 20 | 57.2 | 57.8 | 58.6 | 1.5 | 1.6 | 1.7 |
| 26 | 2 | 1 | 0 | 67.5 | 68.7 | 67.8 | 2.3 | 2.4 | 2.7 |
| 27 | 19 | 26 | 28 | 59.1 | 62.8 | 61.7 | 1 | 1.4 | 1.3 |
| 28 | 24 | 21 | 28 | 62.8 | 61.5 | 63.6 | 4.8 | 2.1 | 4.9 |
| 29 | 22 | 13 | 4 | 56.1 | 54.4 | 54 | 1 | 1.2 | 0.9 |
| 30 | 21 | 27 | 21 | 60.3 | 61.3 | 63.3 | 1.9 | 2.3 | 8.3 |
| 31 | 39 | 36 | 35 | 95.6 | 96.9 | 97.5 | 0.5 | 1.4 | 4 |
| 32 | 23 | 22 | 18 | 50.6 | 49.7 | 52 | 3.8 | 5 | 3.4 |
| 33 | 30 | 12 | 8 | 76.5 | 77.1 | 73.1 | 2.8 | 2.5 | 2.5 |
| 34 | 27 | 23 | 26 | 58.4 | 58.1 | 56.8 | 3.8 | 4.4 | 1.2 |
| 35 | 15 | 20 | 0 | 46.2 | 46.1 | 43.6 | 0.7 | 0.6 | 0.6 |
| 36 | 24 | 24 | 21 | 63.7 | 67.4 | 64.3 | 2.6 | 1.8 | 5 |
| 37 | 13 | 17 | 19 | 66 | 63.8 | 61.1 | 2.7 | 2.4 | 2.8 |
| 38 | 28 | 30 | 13 | 63.3 | 65.1 | 64.4 | 1.1 | 1.4 | 1.1 |
| 39 | 28 | 41 | 43 | 88.4 | 87.5 | 87.4 | 3.1 | 2.1 | 1.5 |
| 40 | 4 | 19 | 36 | 63.1 | 59.6 | 60.2 | 1.9 | 2.7 | 2.9 |

Fig. 8

DATASET A

Clinical Data

| (1) ID | (25) SEX | (26) AGE | (27) HEIGHT | (28) WEIGHT |
|---|---|---|---|---|
| 1 | 1 | 54.45 | 61 | 134 |
| 2 | 1 | 71.93 | 60 | 118 |
| 3 | 0 | 41.63 | 77 | 195 |
| 4 | 1 | 54.43 | 67 | 189 |
| 5 | 0 | 65.35 | 74 | 301 |
| 6 | 0 | 48.22 | 76 | 244 |
| 7 | 1 | 68.03 | 58 | 140 |
| 8 | 0 | 61.95 | 69 | 189 |
| 9 | 1 | 75.97 | 60 | 140 |
| 10 | 0 | 59.49 | 72 | 208 |
| 11 | 1 | 52.31 | 65 | 105 |
| 12 | 0 | 55.47 | 71 | 160 |
| 13 | 0 | 50.68 | 71 | 270 |
| 14 | 0 | 57.16 | 71 | 244 |
| 15 | 1 | 41.19 | 65 | 173 |
| 16 | 1 | 49.72 | 66 | 173 |
| 17 | 1 | 58.59 | 63 | 150 |
| 18 | 0 | 59.82 | 65 | 170 |
| 19 | 1 | 62.43 | 66 | 165 |
| 20 | 1 | 80.3 | 60 | 132 |
| 21 | 0 | 62.14 | 72 | 261 |
| 22 | 1 | 48.21 | 63 | 220 |
| 23 | 1 | 48.53 | 61 | 170 |
| 24 | 1 | 62 | 63 | 135 |
| 25 | 1 | 49.3 | 66 | 204 |
| 26 | 0 | 32.69 | 74 | 260 |
| 27 | 1 | 65.06 | 64 | 177 |
| 28 | 0 | 39.8 | 67 | 175 |
| 29 | 0 | 66.19 | 73 | 324 |
| 30 | 0 | 61.01 | 75 | 223 |
| 31 | 0 | 54.3 | 72 | 170 |
| 32 | 1 | 73.63 | 68 | 182 |
| 33 | 0 | 60.51 | 75 | 256 |
| 34 | 0 | 67.04 | 70 | 200 |
| 35 | 1 | 74.79 | 64 | 136 |
| 36 | 0 | 49.69 | 72 | 212 |
| 37 | 0 | 43.49 | 71 | 259 |
| 38 | 0 | 43.21 | 74 | 230 |
| 39 | 1 | 65.22 | 65 | 165 |
| 40 | 0 | 59.48 | 74 | 218 |

Fig. 9

DATASET B

Disease Status Information

| (1) ID | (2) RCA | (3) LAD | (4) LCX | (5) BP_SYST | (6) BP_DIAS |
|---|---|---|---|---|---|
| 41 | 12 | 15 | 25 | 102 | 55 |
| 42 | 90 | 44 | 26 | 123 | 77 |
| 43 | 16 | 17 | 16 | 144 | 82 |
| 44 | 19 | 28 | 46 | 126 | 58 |
| 45 | 15 | 18 | 10 | 120 | 71 |
| 46 | 8 | 26 | 12 | 137 | 61 |
| 47 | 43 | 60 | 66 | 109 | 51 |
| 48 | 39 | 36 | 34 | 140 | 79 |
| 49 | 12 | 14 | 9 | 122 | 53 |
| 50 | 38 | 55 | 55 | 141 | 53 |

Fig. 10A

DATASET B

Data Derived from Cardiovascular Sound Signals

| (1) ID | (7) BEATS_R | (8) BEATS_C | (9) BEATS_L | (10) FMS_R | (11) FMS_C | (12) FMS_L | (13) S3_R | (14) S3_C | (15) S3_L |
|---|---|---|---|---|---|---|---|---|---|
| 41 | 31 | 31 | 30 | 0.077 | 0 | 0.073 | 12 | 20 | 0 |
| 42 | 32 | 30 | 33 | 0 | 0.012 | 0.017 | 25 | 28 | 20 |
| 43 | 25 | 25 | 24 | 0.118 | 0.238 | 0.081 | 19 | 18 | 9 |
| 44 | 38 | 37 | 38 | 0.137 | 0.012 | 0 | 0 | 6 | 1 |
| 45 | 30 | 31 | 31 | 0 | 0.013 | 0 | 6 | 0 | 0 |
| 46 | 34 | 30 | 14 | 0.023 | 0.068 | 0.171 | 22 | 15 | 13 |
| 47 | 34 | 27 | 29 | 0 | 0.081 | 0.013 | 28 | 11 | 26 |
| 48 | 32 | 31 | 31 | 0.001 | 0.086 | 0.121 | 22 | 17 | 1 |
| 49 | 28 | 28 | 28 | 0 | 0.013 | 0.089 | 8 | 18 | 10 |
| 50 | 25 | 24 | 25 | 0.004 | 0.002 | 0.086 | 1 | 6 | 0 |

Fig. 10B

DATASET B

Data Derived from Cardiovascular Sound Signals

| (1) ID | (16) S4_R | (17) S4_C | (18) S4_L | (19) HR_R | (20) HR_C | (21) HR_L | (22) HRSD_R | (23) HRSD_C | (24) HRSD_L |
|---|---|---|---|---|---|---|---|---|---|
| 41 | 23 | 23 | 0 | 65.1 | 64.8 | 65.2 | 2.5 | 2 | 2.9 |
| 42 | 27 | 27 | 18 | 67.4 | 69 | 68.7 | 1.1 | 2.5 | 3.3 |
| 43 | 25 | 19 | 15 | 54.5 | 54.8 | 54 | 1.5 | 1.3 | 1.3 |
| 44 | 37 | 5 | 6 | 80.3 | 76.8 | 78.3 | 4.4 | 1.1 | 1.2 |
| 45 | 28 | 14 | 31 | 64.8 | 65.6 | 66.7 | 1.5 | 1.8 | 1.1 |
| 46 | 25 | 25 | 12 | 62.6 | 65.5 | 59 | 3.7 | 6.5 | 1.9 |
| 47 | 31 | 26 | 27 | 71.7 | 59.9 | 58.9 | 4.2 | 0.9 | 2.2 |
| 48 | 32 | 22 | 26 | 67 | 67.5 | 66.7 | 1.7 | 1.8 | 1.6 |
| 49 | 24 | 25 | 25 | 59.6 | 60.1 | 60.2 | 0.6 | 1.6 | 0.8 |
| 50 | 2 | 13 | 0 | 53.5 | 55.2 | 55.7 | 2.2 | 1.3 | 1.7 |

Fig. 11A

DATASET B

Clinical Data

| (1) ID | (25) SEX | (26) AGE | (27) HEIGHT | (28) WEIGHT |
|---|---|---|---|---|
| 41 | 0 | 33.97 | 70 | 204 |
| 42 | 0 | 50.91 | 69 | 228 |
| 43 | 0 | 55.46 | 68 | 160 |
| 44 | 1 | 55.09 | 62 | 139 |
| 45 | 0 | 37.01 | 69 | 180 |
| 46 | 1 | 53.6 | 67 | 262 |
| 47 | 0 | 69.68 | 65 | 141 |
| 48 | 0 | 48.25 | 74 | 230 |
| 49 | 0 | 53.33 | 74 | 220 |
| 50 | 1 | 56.38 | 63 | 140 |

Fig. 11B

DESCRIPTIONS OF VARIABLES IN DATASETS A AND B

| Variable | Description |
| --- | --- |
| ID | Subject's unique identification number. |
| RCA | Percentage stenosis in the right coronary artery. |
| LAD | Percentage stenosis in the left anterior descending artery. |
| LCX | Percentage stenosis in the left circumflex artery. |
| BP_SYST | Systolic blood pressure (mmHg). |
| BP_DIAS | Diastolic blood pressure (mmHg). |
| BEATS_R | Number of heartbeats recorded at the right recording location. |
| BEATS_C | Number of heartbeats recorded at the center recording location. |
| BEATS_L | Number of heartbeats recorded at the left recording location. |
| FMS_R | Flow Murmur Score from the right recording location. |
| FMS_C | Flow Murmur Score from the center recording location. |
| FMS_L | Flow Murmur Score from the left recording location. |
| S3_R | Number of S3 sounds recorded at the right recording location. |
| S3_C | Number of S3 sounds recorded at the center recording location. |
| S3_L | Number of S3 sounds recorded at the left recording location. |
| S4_R | Number of S4 sounds recorded at the right recording location. |
| S4_C | Number of S4 sounds recorded at the center recording location. |
| S4_L | Number of S4 sounds recorded at the left recording location. |
| HR_R | Heart rate recorded at the right recording location. |
| HR_C | Heart rate recorded at the center recording location. |
| HR_L | Heart rate recorded at the left recording location. |
| HRSD_R | Heart rate standard deviation recorded at the right recording location. |
| HRSD_C | Heart rate standard deviation recorded at the center recording location. |
| HRSD_L | Heart rate standard deviation recorded at the left recording location. |
| SEX | 0=Female, 1=Male. |
| AGE | Age (years). |
| HEIGHT | Height (in.). |
| WEIGHT | Weight (lbs.). |

Fig. 12

Example I: Parameter Estimates, Probabilities, and
Updated Parameter Estimates for a Logit Model of Hypertension Model:

$$\Pr(Y = 1 \mid X, \omega = \{\beta\}) = \Lambda(\beta_0 + \beta_1 AVGHR + \beta_2 AVGHRSD + \beta_3 AVGS4 + \beta_4 AGE)$$

Variable Descriptions:

| | |
|---|---|
| Y | Binomial indicator of hypertension: |
| | Y=0     Hypertension is not present. |
| | Y=1     Hypertension is present. |
| AVGHR | Average heart rate over all recording locations. |
| AVGHRSD | Average heart rate standard deviation over all recording locations. |
| AVGS4 | Average number of S4 sounds recorded per beat over all recording locations. |
| AGE | Age. |

Restrictions:

Males only.

Parameter Estimates:

| | |
|---|---|
| $b_0$ | -0.039 |
| $b_1$ | -0.013 |
| $b_2$ | 0.408 |
| $b_3$ | -9.133 |
| $b_4$ | 0.081 |

Fig. 13

Example I: Parameter Estimates, Probabilities, and
Updated Parameter Estimates for a Logit Model of Hypertension Predictions:

(Note: Predictions are not generated for those subjects not satisfying the restrictions.)

| ID | $Pr(Y=0 \mid X, w=\{b\})$ | $Pr(Y=1 \mid X, w=\{b\})$ |
|---|---|---|
| 41 | . | . |
| 42 | . | . |
| 43 | . | . |
| 44 | 0.388 | 0.612 |
| 45 | . | . |
| 46 | 0.905 | 0.095 |
| 47 | . | . |
| 48 | . | . |
| 49 | . | . |
| 50 | 0.068 | 0.932 |

Updated Parameter Estimates:

| | |
|---|---|
| $b_0$ | -1.685 |
| $b_1$ | -0.014 |
| $b_2$ | 0.208 |
| $b_3$ | -2.960 |
| $b_4$ | 0.045 |

Fig. 14

Example II: Parameter Estimates, Probabilities, and
Updated Parameter Estimates for an Alternative Logit Model of Hypertension Model:

$$\Pr(Y = 1 \mid X, \omega = \{\beta\}) = \Lambda(\beta_0 + \beta_1 AVGHR + \beta_2 AVGHRSD + \beta_3 AVGS4 + \beta_4 AGE)$$

Variable Descriptions:

| | | |
|---|---|---|
| Y | Binomial indicator of hypertension: | |
| | Y=0 | Hypertension is not present. |
| | Y=1 | Hypertension is present. |
| AVGHR | Average heart rate over all recording locations. | |
| AVGHRSD | Average heart rate standard deviation over all recording locations. | |
| AVGS4 | Average number of S4 sounds recorded per beat over all recording locations. | |
| AGE | Age. | |

Restrictions:
    Males only.

Parameter Estimates:

| | |
|---|---|
| $b_0$ | -0.473 |
| $b_1$ | 0.004 |
| $b_2$ | 0.233 |
| $b_3$ | -8.192 |
| $b_4$ | 0.068 |

Fig. 15

Example II: Parameter Estimates, Probabilities, and
Updated Parameter Estimates for an Alternative Logit Model of Hypertension Predictions:

(Note: Predictions are not generated for those subjects not satisfying the restrictions.)

| ID | $Pr(Y=0 \mid X, w=\{b\})$ | $Pr(Y=1 \mid X, w=\{b\})$ |
|----|---------------------------|---------------------------|
| 41 | . | . |
| 42 | . | . |
| 43 | . | . |
| 44 | 0.350 | 0.650 |
| 45 | . | . |
| 46 | 0.908 | 0.092 |
| 47 | . | . |
| 48 | . | . |
| 49 | . | . |
| 50 | 0.095 | 0.905 |

Updated Parameter Estimates:

| | |
|---|---|
| $b_0$ | -1.846 |
| $b_1$ | -0.013 |
| $b_2$ | 0.166 |
| $b_3$ | -1.790 |
| $b_4$ | 0.037 |

Fig. 16

Example III: Parameter Estimates, Probabilities, and Updated
Parameter Estimates for a Probit Model of Early-Stage Coronary Artery Disease Model:

$$\Pr(Y = 1 \mid X, \omega = \{\beta\}) = \Phi(\beta_0 + \beta_1 FMS\_R + \beta_2 FMS\_C + \beta_3 FMS\_L + \beta_4 AVGS3 + \beta_5 BMI)$$

Variable Descriptions:

| | |
|---|---|
| Y | Binomial indicator of early-stage coronary artery disease: |
| | Y=0    Early-stage coronary artery disease is not present. |
| | Y=1    Early-stage coronary artery disease is present. |
| FMS_R | Flow Murmur Score at the right recording location. |
| FMS_C | Flow Murmur Score at the center recording location. |
| FMS_L | Flow Murmur Score at the left recording location. |
| AVGS3 | Average number of S3 sounds recorded per beat over all recording locations. |
| BMI | Body-mass index. |

Restrictions:

No more than 60 years of age only.

Parameter Estimates:

| | |
|---|---|
| $b_0$ | -5.991 |
| $b_1$ | -11.919 |
| $b_2$ | 19.182 |
| $b_3$ | 20.160 |
| $b_4$ | 2.448 |
| $b_5$ | 0.090 |

Fig. 17

Example III: Parameter Estimates, Probabilities, and Updated
Parameter Estimates for a Probit Model of Early-Stage Coronary Artery Disease Predictions:

(Note: Predictions are not generated for those subjects not satisfying the restrictions.)

| ID | $Pr(Y=0 \mid X, w=\{b\})$ | $Pr(Y=1 \mid X, w=\{b\})$ |
|----|---------------------------|---------------------------|
| 41 | 0.976 | 0.024 |
| 42 | 0.695 | 0.305 |
| 43 | 0.006 | 0.994 |
| 44 | 1.000 | 0.000 |
| 45 | 0.999 | 0.001 |
| 46 | 0.000 | 1.000 |
| 47 |       |       |
| 48 | 0.039 | 0.961 |
| 49 | 0.644 | 0.356 |
| 50 | 0.965 | 0.035 |

Updated Parameter Estimates:

| | |
|---|---|
| $b_0$ | -2.201 |
| $b_1$ | -1.612 |
| $b_2$ | 4.813 |
| $b_3$ | 5.574 |
| $b_4$ | -2.155 |
| $b_5$ | 0.075 |

Fig. 18

Example IV: Parameter Estimates, Probabilities, and Updated
Parameter Estimates for an Ordered Probit Model of Coronary Artery Disease Model:

$$\Pr(Y = 0 \mid X, \omega = \{\beta\}) = \Phi(-\beta_0 - \beta_1 FMS\_R - \beta_2 FMS\_C - \beta_3 FMS\_L - \beta_4 AVGS3 - \beta_5 BMI)$$

$$\Pr(Y = 0 \mid X, \omega = \{\beta\}) = \Phi(\mu_1 - \beta_0 - \beta_1 FMS\_R - \beta_2 FMS\_C - \beta_3 FMS\_L - \beta_4 AVGS3 - \beta_5 BMI)$$
$$- \Phi(-\beta_0 - \beta_1 FMS\_R - \beta_2 FMS\_C - \beta_3 FMS\_L - \beta_4 AVGS3 - \beta_5 BMI)$$

$$\Pr(Y = 2 \mid X, \omega = \{\beta\}) = 1 - \Phi(\mu_1 - \beta_0 - \beta_1 FMS\_R - \beta_2 FMS\_C - \beta_3 FMS\_L - \beta_4 AVGS3 - \beta_5 BMI)$$

Variable Descriptions:

| | |
|---|---|
| Y | Trinomial indicator of coronary artery disease: |
| Y=0 | Coronary artery disease is not present. |
| Y=1 | Mild coronary artery disease is present. |
| Y=2 | Significant coronary artery disease present. |
| FMS_R | Flow Murmur Score at the right recording location. |
| FMS_C | Flow Murmur Score at the center recording location. |
| FMS_L | Flow Murmur Score at the left recording location. |
| AVGS3 | Average number of S3 sounds recorded per beat over all recording locations. |
| BMI | Body-mass index. |

Restrictions:

No more than 60 years of age only.

Parameter Estimates:

| | | | |
|---|---|---|---|
| $b_0$ | -3.443 | $m_1$ | 1.533 |
| $b_1$ | -9.458 | | |
| $b_2$ | 17.511 | | |
| $b_3$ | 9.102 | | |
| $b_4$ | 1.997 | | |
| $b_5$ | 0.037 | | |

Fig. 19

Example IV: Parameter Estimates, Probabilities, and Updated
Parameter Estimates for an Ordered Probit Model of Coronary Artery Disease Predictions:

(Note: Predictions are not generated for those subjects not satisfying the restrictions.)

| ID | $Pr(Y=0 \mid X, w=\{b, m\})$ | $Pr(Y=1 \mid X, w=\{b, m\})$ | $Pr(Y=2 \mid X, w=\{b, m\})$ |
|---|---|---|---|
| 41 | 0.958 | 0.041 | 0.001 |
| 42 | 0.609 | 0.356 | 0.035 |
| 43 | 0.006 | 0.163 | 0.831 |
| 44 | 1.000 | 0.000 | 0.000 |
| 45 | 0.982 | 0.018 | 0.000 |
| 46 | 0.023 | 0.297 | 0.680 |
| 47 |  |  |  |
| 48 | 0.135 | 0.532 | 0.333 |
| 49 | 0.689 | 0.289 | 0.002 |
| 50 | 0.939 | 0.060 | 0.001 |

Updated Parameter Estimates:

| | | | |
|---|---|---|---|
| $b_0$ | -2.036 | $m_1$ | 1.122 |
| $b_1$ | -2.042 | | |
| $b_2$ | 5.229 | | |
| $b_3$ | 2.826 | | |
| $b_4$ | -0.744 | | |
| $b_5$ | -0.058 | | |

Fig. 20

METHOD AND SYSTEM FOR MODELING CARDIOVASCULAR DISEASE USING A PROBABILITY REGRESSION MODEL

FIELD OF THE INVENTION

The present invention generally relates to methods and systems for modeling cardiovascular disease using a probability regression model.

BACKGROUND

The cardiovascular system generates a rich assortment of normal and abnormal physiological sounds. The abnormal sounds are usually indicative of one or more cardiovascular diseases. A mode of diagnosing cardiovascular diseases using cardiovascular sounds is of great benefit because sound detection poses minimal risk to a subject being diagnosed. Traditional clinical auscultation, of course, has been used in this manner, but this mode is limited in that it cannot detect sounds that are outside the normal human auditory range or those that are obscured by normal physiological sounds. Indeed, several sounds indicative of cardiovascular disease fall into these categories.

One general methodology that has been proposed to overcome this difficulty is to use a digital stethoscope device to record cardiovascular sounds and then to apply signal-processing techniques to identify the audible and sub-audible features of interest present in the recorded cardiovascular sound signals. These features of interest, in turn, can either directly or indirectly serve as discriminants between the normal and abnormal cardiovascular sounds, and hence they can indicate or contraindicate cardiovascular diseases. For example, discriminating between normal and abnormal cardiovascular sounds is often performed by selecting features of interest from a mathematical model of the cardiovascular sound signals.

Unfortunately, the discriminatory power of such prior techniques has proved weaker than desired for some applications. Moreover, better capability for identifying predictors of cardiovascular disease and/or determining a probability of cardiovascular disease is desired.

SUMMARY

In light of the difficulties inherent in the prior methods, one or more embodiments of the present invention provide a method and system for modeling cardiovascular disease using a probability regression model.

In accordance with an embodiment, a parameter estimate of a probability regression model for cardiovascular disease is generated using disease status information and predictors derived from cardiovascular sound signals.

In accordance with another embodiment, a probability of cardiovascular disease is generated using a probability regression model that includes a predictor derived from cardiovascular sound signals.

Other advantages and features associated with one or more embodiments of the present invention will become more readily apparent to those skilled in the art from the following detailed description. As will be realized, the invention is capable of other and different embodiments than those explicitly discussed below, and its several details are capable of modification in various aspects, all of which can be incorporated without departing from the invention. Accordingly, the drawings and the description that follow are to be regarded as illustrative in nature, and not limiting.

BRIEF DESCRIPTION OF THE DRAWINGS

FIGS. 6-9 provide an example Dataset A that can be used to generate a parameter estimate of a probability regression model of cardiovascular disease.

FIGS. 10-11 provide an example Dataset B that can be used to generate a probability of cardiovascular disease using a probability regression model of cardiovascular disease, and can also be used to update a parameter estimate of a probability regression model of cardiovascular disease.

FIG. 12 provides descriptions of variables in Dataset A and Dataset B.

FIGS. 13-14 provide examples of parameter estimates, probabilities, and updated parameter estimates for a logit model of hypertension, according to an embodiment of the invention illustrated by an Example I.

FIGS. 15-16 provide examples of parameter estimates, probabilities, and updated parameter estimates for an alternative logit model of hypertension, according to an embodiment of the invention illustrated by an Example II.

FIGS. 17-18 provide examples of parameter estimates, probabilities, and updated parameter estimates for a probit model of early-stage coronary artery disease, according to an embodiment of the invention illustrated by an Example III.

FIGS. 19-20 provide examples of parameter estimates, probabilities, and updated parameter estimates for an ordered probit model of coronary artery disease, according to an embodiment of the invention illustrated by an Example IV.

DETAILED DESCRIPTION

Probability Regression Modeling for Cardiovascular Disease

Figure 1:
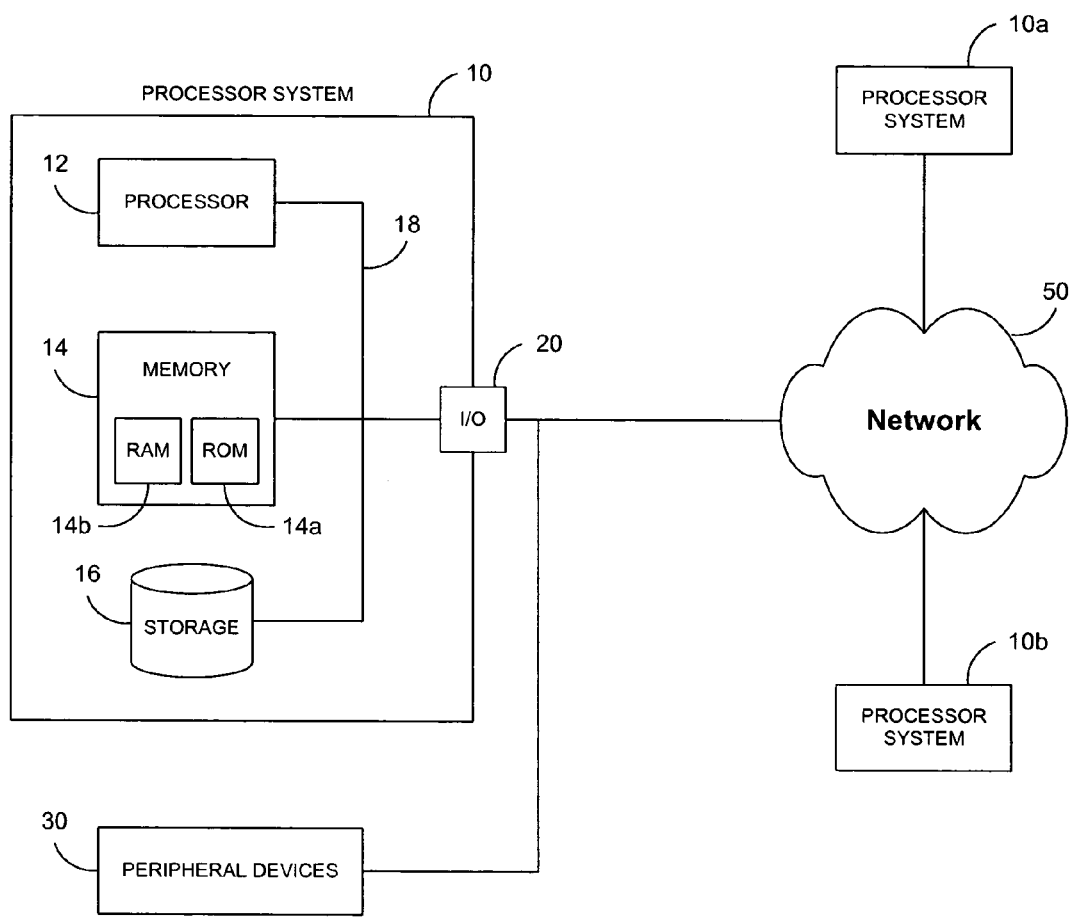
FIG. 1 is a block diagram of a processor system that can be used to model cardiovascular disease using a probability regression model according to an embodiment of the invention.

Embodiments of the present invention model cardiovascular disease using a probability regression model. As used herein, a probability regression model is a regression model in which the outcome is a probability. A probability is derived from a distribution function; functions that qualify as distribution functions are those that satisfy Kolmogorov's Axioms. The general form of such a model is as follows:

$$Pr(Y|X, \omega) = F(X, \omega), \qquad \text{Eq. 1}$$

where Y is the event of interest to be predicted by the model (which will usually be interpreted as a scalar or a vector), F is a distribution function, X is a set of predictors (which will usually be interpreted as a vector or a matrix), and $\omega$ is a set of parameters (which will usually be interpreted as one or more scalars or vectors). The interpretation of $Pr(Y|X, \omega)$ is thus the probability of the event of interest Y, given predictors X and parameters $\omega$. Descriptions of Y, F, X, and $\omega$ in the context of modeling cardiovascular disease follow.

Description of the Event of Interest Y

The general form of a probability regression model in Eq. 1 permits several formulations of the event of interest Y, which is in embodiments of this invention a cardiovascular disease event. The formulations of the event of interest Y are most often in the classes of limited dependent variables, discrete dependent variables, or survival dependent variables, which are often modeled using a probability regression model.

One formulation of Y is a binomial event. For example, if the cardiovascular disease is congestive heart failure, then a binomial formulation of Y can be constructed as follows:

$$Y = \begin{cases} 0 & \text{if congestive heart failure is not present} \\ 1 & \text{if congestive heart failure is present} \end{cases}.$$

In applications of probability regression models that use this formulation, it is typically assumed that the two categories are mutually exhaustive. This assumption can be actually true in some cases, or a reasonable approximation in others.

Another formulation of Y is a survival time until an event occurs, i.e., a duration of survival. For example, if the cardiovascular disease is congestive heart failure, then a survival-time formulation of Y can be constructed as follows:

Y=time until death from congestive heart failure.

Yet another formulation of Y is an ordered multinomial event. For example, if the cardiovascular disease is congestive heart failure, then an ordered multinomial formulation of Y can be constructed as follows:

$$Y = \begin{cases} 0 & \text{if congestive heart failure is not present} \\ 1 & \text{if mild congestive heart failure is present} \\ 2 & \text{if moderate congestive heart failure is present} \\ 3 & \text{if severe congestive heart failure is present} \end{cases}.$$

In applications of probability regression models which use this formulation, it is typically assumed that the multiple categories are mutually exhaustive. This assumption can be actually true in some cases, or a reasonable approximation in others.

Yet another formulation of Y is an unordered multinomial event. For example, if the cardiovascular disease is congestive heart failure, then an unordered multinomial formulation of Y can be constructed as follows:

$$Y = \begin{cases} 0 & \text{if congestive heart failure is not present} \\ 1 & \text{if congestive heart failure arises} \\ & \text{from left bundle branch block} \\ 2 & \text{if congestive heart failure arises} \\ & \text{from right bundle branch block} \end{cases}.$$

In applications of probability regression models that use this formulation, it is typically assumed that the multiple categories are mutually exclusive. This assumption can be actually true in some cases, or a reasonable approximation in others.

Examples of cardiovascular diseases that can be modeled in accordance with embodiments of the present invention include, but are not necessarily limited to, the following: acute alcoholic hepatitis; acute rheumatic fever (Carey Coombs murmur); anemia; aortic insufficiency (Austin Flint murmur); arteriovenous fistula (systemic or pulmonic); atrial myxoma; atrial septal aneurysm; atrial septal defect; atrioventricular junctional rhythm; bacterial endocarditis; bundle branch block; branch pulmonary stenosis; carotid occlusion; celiac mesenteric occlusion; chronic cor pulmonale; coarctation of aorta; complete heart block; congenital heart disease; high-to-low pressure shunts; rapid blood flow; secondary to localized arterial obstruction; cor triatriatum; coronary artery disease; coronary heart disease; coronary occlusion; diffuse endomyocardial disease; Ebstein's malformation; femoral occlusion; heart trauma, direct or indirect; hemiangioma; hpyerthyroidism; hyperemia of neoplasm (hepatoma renal cell carcinoma, Paget's disease); hypertensive heart disease; hyperthyroidism; hypertrophic cardiomyopathy; hypertrophic subaortic stenosis; intercostal muscle contractions; intraventricular tumors or other masses; left atrial tumor; left-to-right atrial shunting (Lutembacher's syndrome, mitral atresia plus atrial septal defect); mammary souffle; marfan syndrome; mediastinal emphysema; membraneous ventricular septal aneurysm; mitral commisurotomy; mitral insufficiency; mitral stenosis; mitral valve prolapse; myocarditis nylon chordae; papillary muscle dysfunction; pericardial effusion; pericardial heart disease; pleural or pericardial adhesions; pneumoperitoneum; pneumothorax; polyarteritis nodosa; pulmonary septal defect (patent ductus arteriosus); renal occlusion; spontaneous closure of ventricular septal defects; systemic artery to pulmonary artery (patent ductus arterious, aortopulmonary window, truncus arteriosus, pulmonary atresia, anomalous left coronary, bronchiectasis, sequestration of the lung); systemic artery to right heart (ruptured sinus of Valsalva, coronary artery fistula); systemic lupus erythematosus; torn porcine valve cusps; tricuspid valve prolapse; venous hum; venovenous shunts (anomalous pulmonary veins, portosystemic shunts); and ventricular septal defect.

Description of the Distribution Function F

Referring again to the general form of a probability regression model in Eq. 1, the choice of functional form for the distribution function F depends primarily upon the formulation of the event of interest Y, which is a cardiovascular disease event, according to one or more embodiments of the invention. Specific examples of choices of the distribution function F applicable to each of the above-mentioned formulations of the event of interest Y are set forth below. It should be noted that some probability regression models are formulated in terms of the cumulative, i.e., integrated, distribution function; the cases in which F represents a cumulative distribution function will be apparent given the mathematical form of the model.

First, if Y is formulated as a binomial cardiovascular disease event, the following probit model, which is based on the normal distribution function, can be used:

$$Pr(Y = 1 | X, \omega = \{\beta, \sigma\}) = \frac{1}{\sqrt{2\pi\sigma^2}} \int_{s=-\infty}^{X'\beta} \exp\left(-\frac{s^2}{2\sigma^2}\right) ds \equiv \Phi\left(\frac{X'\beta}{\sigma}\right),$$ Eq. 2 where $\Phi(\cdot)$ denotes the standard normal cummulative distribution function, and "'" denotes the transpose of a vector or matrix. $Pr(Y=1|X, \omega=\{\beta, \sigma\})$ is the probability of the binomial event being $Y=1$; the probability of the binomial event being $Y=0$ can be easily found by the equation $Pr(Y=0|X, \omega=\{\beta, \sigma\})=1-Pr(Y=1|X, \omega=\{\beta, \sigma\})$. The probability $Pr(Y=1|X, \omega=\{\beta, \sigma\})$ is completely determined once predictors X and parameters $\omega=\{\beta, \sigma\}$ are known. In most applications of the probit model, including the examples presented below, the parameter $\sigma$ is normalized to 1.

Additional probability regression models that can be used if Y is formulated as a binomial cardiovascular disease event include the logit model and the linear model.

Second, if Y is formulated as a survival time until a cardiovascular disease event occurs, the following Weibull model, which is based on the Weibull distribution function, can be used:

$$Pr(Y|X, \omega = \{\beta, \sigma\}) = \exp\left(-\exp\left(\frac{\ln(Y) - X'\beta}{\sigma}\right)\right).$$ Eq. 3

$Pr(Y|X, \omega=\{\beta, \sigma\})$ is the probability of surviving the event until at least time Y. For any particular survival time Y, the probability $Pr(Y|X, \omega=\{\beta, \sigma\})$ is completely determined once predictors X and parameters $\omega=\{\beta, \sigma\}$ are known.

Additional probability regression models that can be used if Y is formulated as a survival time until a cardiovascular disease event occurs include the Cox proportional hazards model, the exponential model, the log-logistic model, the lognormal model, and the Kaplan-Meier model.

Third, if Y is formulated as an ordered multinomial cardiovascular disease event with categories $0, 1, 2, \ldots, J$, where the categories are defined by bounds $\mu=\{\mu_0, \mu_1, \mu_2, \ldots, \mu_{J-1}\}$, then the following ordered probit model, which is based on the normal distribution function, can be used:

$$Pr(Y = 0 | \omega = \{\beta, \sigma, \mu\}) = \Phi\left(\frac{\mu_0 - X'\beta}{\sigma}\right) \quad \text{if } Y = 0$$ Eq. 4

$$Pr(Y = j | \omega = \{\beta, \sigma, \mu\}) = \quad \text{if } Y = 1, 2, \ldots, J-1$$

$$\Phi\left(\frac{\mu_j - X'\beta}{\sigma}\right) - \Phi\left(\frac{\mu_{j-1} - X'\beta}{\sigma}\right)$$

$$Pr(Y = J | \omega = \{\beta, \sigma, \mu\}) = 1 - \quad \text{if } Y = J.$$

$$\Phi\left(\frac{\mu_{J-1} - X'\beta}{\sigma}\right)$$

$Pr(Y=j|X, \omega=\{\beta, \sigma, \mu\})$ is the probability of the ordered multinomial event being $Y=j$. The probability $Pr(Y=j|X, \omega=\{\beta, \sigma, \mu\})$ is completely determined for each category j once predictors X and parameters $\omega=\{\beta, \sigma, \mu\}$ are known. In most applications of the ordered probit model, including the examples presented below, the parameter $\sigma$ is normalized to 1, and the initial bound $\mu_0$ is normalized to 0.

Additional probability regression models that can be used if Y is formulated as an ordered multinomial cardiovascular disease event include the ordered logit model and the linear model.

Fourth, if Y is formulated as an unordered multinomial cardiovascular disease event with categories $0, 1, 2, \ldots, J$, then the following multinomial logit model, which is based on the extreme-value (type I) distribution function, can be used:

$$Pr(Y = j | X, \omega = \{\beta, \theta, \lambda\}) = 1 - \exp\left(-\exp\left(\frac{X'\beta_j - \theta}{\lambda}\right)\right).$$ Eq. 5

$Pr(Y=j|X, \omega=\{\beta, \theta, \lambda\})$ is the probability of the unordered multinomial event being $Y=j$, and $\beta_j$ is the subset of $\beta$ corresponding to category j. The probability $Pr(Y=j|X, \omega=\{\beta, \theta, \lambda\})$ is completely determined for each category j once predictors X and parameters $\omega=\{\beta, \theta, \lambda\}$ are known. In most applications of the multinomial logit model, including the examples presented below, the parameter $\theta$ is normalized to 0, the parameter $\lambda$ is normalized to 1, and each set of parameters $\beta_j$ are normalized by differencing them from $\beta_0$ (effectively setting $\beta_0=0$).

Once this last normalization is applied, the distribution function for the multinomial logit model becomes $$Pr(Y = j | X, \omega = \{\beta, \theta, \lambda\}) = \frac{\exp\left(\frac{X'\beta_j - \theta}{\lambda}\right)}{1 + \sum_{k=1}^{J} \exp\left(\frac{X'\beta_k - \theta}{\lambda}\right)} \equiv \Lambda\left(\frac{X'\beta_j - \theta}{\lambda}\right),$$ Eq. 6 where $\Lambda(\cdot)$ denotes the standard logistic cummulative distribution function.

Additional probability regression models that can be used if Y is formulated as an unordered multinomial cardiovascular disease event include the multinomial probit model, the generalized extreme value model, the nested probit model, and the nested logit model.

In accordance with other embodiments, functional forms of the distribution function F other than those set forth above can be used, depending on their particular suitabilities for modeling the cardiovascular disease event of interest Y.

Description of the Predictors X

The predictors X are any data that can be used to predict the event of interest Y, which is in embodiments of this invention a cardiovascular disease event. In embodiments of this invention, the predictors X can be of two types, data derived from cardiovascular sound signals and optional clinical data, each of which has correlation with cardiovascular disease, and preferably some causative relationship with cardiovascular disease.

For example, the predictors X can include clinical data, which include any data that can be in a subject's, e.g., a person's or a patient's, medical record. Examples of clinical data include the following:

(1) Physical descriptors, e.g., height, weight, blood pressure, body mass index, morphological characteristics;

(2) Demographics, e.g., ethnicity, sex, age, socioeconomic classification;

(3) History of disease, e.g., family history of disease, subject history of disease;

(4) Results of diagnostic tests, e.g., results of a cholesterol test, results of a C-reactive protein test, results of an electrocardiogram monitoring, results of an exercise stress test, results of a catheterization analysis, results of an echocardiographic analysis, results of an electron-beam computed tomography analysis, results of a magnetic resonance imaging analysis;

(5) Prior surgeries or interventions, e.g., coronary angiographic bypass graft, stent placement, balloon angioplasty;

(6) Current or past medications, e.g., aspirin, statins, hormone replacement therapy; and (7) Habits, e.g., number of cigarettes smoked per day, number of alcoholic drinks taken per day, amount of fat in the diet.

Nearly all of the above examples of clinical data have a demonstrable correlation (either positive or negative) with specific types of cardiovascular disease. Some well-documented examples include the following:

(1) The body-mass index is correlated with incidence of myocardial infarction;

(2) Those subjects with lower income often have comparatively higher mortality rates from coronary heart disease;

(3) Family history of stroke is highly correlated with the early onset of stroke;

(4) Bundle branch block will frequently present in an anomalous electrocardiogram;

(5) Those subjects who have undergone a coronary angiographic bypass graft are at relatively higher risk for coronary restenosis;

(6) The drug Sildenafil in conjunction with nitrates can cause hypotension; and (7) Heavy drinking is correlated with increased risk of arrhythmia.

As mentioned above, the predictors X also can include data generated, i.e., derived, from cardiovascular sound signals. A cardiovascular sound is a sound emanating from the cardiovascular system of a subject, including sounds emanating from a subject's heart and blood vessels. A cardiovascular sound signal is a physical representation of a cardiovascular sound using a medium that can be varied in order to convey information about the cardiovascular sound.

Examples of common normal and abnormal cardiovascular sounds include the following:

(1) Normal sounds, e.g., S1, S2;

(2) Abnormal heart valve sounds, e.g., regurgitation, mid-systolic click, split S1;

(3) Abnormal atrial and ventricular sounds, e.g., ventricular gallop (S3), atrial gallop (S4);

(4) Vascular bruits, e.g., renal bruit, coronary bruit, carotid bruit;

(5) Innocent murmurs, e.g., Still's murmur, venous hum;

(6) Pathological murmurs, e.g., systolic ejection murmur; and (7) Abnormal duration of sounds, e.g., high heart rate variability, short diastolic interval.

Some well-documented examples of cardiovascular diseases or proper functions that can be indicated by the above cardiovascular sounds include the following:

(1) The S1 and S2 are both normal heart sounds;

(2) A mid-systolic click can indicate mitral valve prolapse;

(3) A ventricular gallop (S3) can indicate congestive heart failure;

(4) A carotid bruit can indicate atherosclerosis in the carotid artery;

(5) A venous hum is a normal sound often generated in a child's jugular vein;

(6) A systolic ejection murmur can indicate atrial septal defect; and (7) High heart rate variability can indicate hypertension.

Cardiovascular sounds can be either auscultatable, i.e., able to be heard with the human ear, or non-auscultatable. Auscultatable cardiovascular sounds are typically heard by a physician using a standard stethoscope, or using a stethoscope with external sound amplification. In embodiments of this invention, the auscultator's assessment of cardiovascular sounds can be utilized when forming predictors X.

However, cardiovascular sounds generated by cardiovascular diseases are often non-auscultatable. This is typically due to one or more of the following causes: (a) the turbulence generated in the cardiovascular system by these diseases is not strong enough to create a sound that exceeds the threshold of audibility, (b) the frequency of the pathological sounds is outside the human auditory range, or (c) the pathological sounds are masked by normal physiological sounds.

A common technique for identifying non-auscultatable, pathological cardiovascular sounds (and also for identifying cardiovascular sounds generally) is to generate cardiovascular sound signals from cardiovascular sounds using a machine, and then to apply a discrimination technique to the cardiovascular sound signals to determine whether or not a particular pathological cardiovascular sound is present. The most common mode of discrimination is to first construct a mathematical model of the cardiovascular sound signals, and then to use some feature of this model as an indicator of whether a specific type of pathological cardiovascular sound is present. When a machine is used to perform this task, the two most common methods of generating cardiovascular sound signals are to create analog or digital recordings of the cardiovascular sounds. Descriptions of some machines that perform these tasks follow.

One machine that performs the task of generating cardiovascular sound signals from cardiovascular sounds is the phonocardiogram. Early formulations of this machine use an analog recording device to generate cardiovascular sound signals. This recording can then be replayed to allow for a more thorough auscultative assessment, or, more frequently, it can be used to generate a graphical time-series plot of the frequencies present in the cardiovascular sound signals. A simple discrimination technique that can be used with this formulation of the phonocardiogram is to visually inspect this plot for time/frequency coincidences corresponding to cardiovascular sounds of interest.

Most modern machines for performing the recording and discrimination tasks are, in essence, enhancements to the original phonocardiogram. One such enhancement is the use of acoustic transducers that are specifically sensitive to the cardiovascular sounds of interest. Using these transducers allows very faint cardiovascular sounds, which are often those of greatest interest, to be more reliably detected. Examples of acoustic transducer enhancements designed for cardiovascular sounds include that described in U.S. Pat. No. 6,478,744 and that described in U.S. Pat. No. 5,109,863, the entire disclosures of which are hereby incorporated by reference.

Another enhancement is the use of mathematical models of the cardiovascular sound signals. Using a mathematical model of the cardiovascular sound signals increases the ability to reliably identify specific cardiovascular sounds, particularly the non-auscultatable cardiovascular sounds, so long as the cardiovascular sound signal is indeed well represented by a particular mathematical model. One example of a mathematical model of the cardiovascular sound signal is a spectral analysis. Most generally, in a spectral analysis, the cardiovascular sound signals are modeled as time series of frequency and power measurements of cardiovascular sounds. For example, U.S. Pat. No. 5,036,857, the entire disclosure of which is hereby incorporated by reference, describes a system that uses an autoregressive, moving-average model to identify a feature of interest present in a heart sound signal. (While an autoregressive, moving-average model is not explicitly a spectral analysis, a simple functional transformation can effect its conversion to a spectral analysis.) As another example, U.S. Pat. No. 5,638,823, the entire disclosure of which is hereby incorporated by reference, describes a system that uses a wavelet model to identify a feature of interest present in a heart sound signal. As yet another example, U.S. Patent Application Publication No. 2003/0229289, the entire disclosure of which is hereby incorporated by reference, describes a system that uses a fast Fourier model to identify a feature of interest present in a cardiovascular sound signal. As yet another example, U.S. Pat. No. 6,572,560, the entire disclosure of which is hereby incorporated by reference, describes a system that uses a neural network to identify a feature of interest present in a heart sound signal.

The cardiovascular sound signal need not be modeled solely in terms of a time series of the frequency and power measurements of cardiovascular sounds as in the spectral analysis, but this is the most common method. In embodiments of this invention, the data derived from cardiovascular sound signals using systems such as the ones listed above are used when forming predictors X.

It should be noted that some data derived from cardiovascular sound signals can be better suited for use in a probability regression model of a particular cardiovascular disease than other data derived from the same cardiovascular sound signals. Examples of data derived from cardiovascular sound signals that can be used in a probability regression model of cardiovascular disease include the following:

(1) Indications of normal cardiovascular sounds, e.g., indications of an S1 or an S2;
(2) Power and frequency measurements of cardiovascular sounds, e.g., the peak power in an S1, the total energy in the carotid upstroke, the peak frequency of a renal bruit;
(3) Timing measurements of cardiovascular sounds, e.g., the duration of an S1, the duration of the diastolic interval relative to the duration of the total heart cycle, the variability in the heart cycle;
(4) Indications of abnormal valvular sounds, e.g., indications of a mid-systolic click, indications of a split S1;
(5) Indications of abnormal atrial or ventricular sounds, e.g., indications of an atrial gallop (S3), indications of a ventricular gallop (S4);
(6) Indications of murmurs, e.g., indications of a systolic ejection murmur; and
(7) Indications of cardiovascular bruits, e.g., indications of a coronary bruit.

As stated above, clinical data and data derived from cardiovascular sound signals can be selected for use as predictors X in a probability regression model of cardiovascular disease because these data are correlated with cardiovascular disease. However, clinical data and data derived from cardiovascular sound signals can also be selected for use in predictors X because these data can control for confounding factors that might be present in other predictors X. For example, clinical data including a description of the quantity of chest hair can be collected for male subjects to control for sounds which might be interpreted as cardiovascular sounds but are actually sounds generated by surface friction between a microphone or other device used to record the cardiovascular sounds and a subject's skin. As another example, clinical data including a description of the breast size can be collected for female subjects to control for alterations in cardiovascular sounds which might occur when the sounds pass through breast tissues of differing densities and/or thicknesses. As yet another example, clinical data including a description of the morphology of the chest can be collected to control for the quality of contact between a microphone or other device used to record the cardiovascular sounds and a subject's skin. As yet another example, data derived from cardiovascular sound signals which include the peak power in the diastolic interval can be collected to control for differences in the quality of a recording of the cardiovascular sound.

Description of the Parameters ω

The above examples of probability regression models illustrate that the probability Pr(Y|X, ω) defined in Eq. 1 is completely determined once the predictors X and the parameters ω are known. However, in most applications, only the predictors X are known; the true values of the parameters ω will typically be unknown. An appeal to the theory of the particular cardiovascular disease being modeled can, in some cases, provide insight into the true values of the parameters ω; but if there is no theoretical intuition available, then some estimate of ω can be substituted. These parameter estimates will be denoted w to distinguish them from the true but unknown parameters ω, i.e., w is a set of estimates of ω (which will usually be interpreted as one or more scalars or vectors). Given a dataset of N observations containing data on both Y and X, it is possible to generate w in several ways. It should be noted that no analytical methodology for generating w is typically available (except for highly idealized cases of the distribution function F), so an iterative, numerical solution methodology is most often used in practice to generate w.

The most common method of estimating w is the method of maximum likelihood, which is defined by the following maximization equation:

$$w = \arg \max_{\omega} \ln[L(Y|X, \omega)], \quad \text{Eq. 7}$$

where $\ln[L(Y|X, \omega)]$ is the log-likelihood function implied by the probability regression model.

For example, log-likelihood functions corresponding to the probability regression models specified by Eq. 2, Eq. 3, Eq. 4, and Eq. 5, respectively, are as follows:

$$\ln[L(Y|X, \omega = \{\beta\})] = \sum_{i=1}^{N} 1(Y_i = 1)\ln[\Phi(X_i'\beta)] + 1(Y_i = 0)\ln[1 - \Phi(X_i'\beta)], \quad \text{Eq. 8}$$

-continued $$\ln[L(Y|X, \omega = \{\beta, \alpha\})] = \qquad \text{Eq. 9}$$
$$\sum_{i=1}^{N} 1(\text{subject } i \text{ survives}) \left[ \frac{\ln(Y_i) - X_i'\beta}{\sigma} - \ln(\sigma) \right],$$
$$-\exp\left[ \frac{\ln(Y_i) - X_i'\beta}{\sigma} \right],$$

$$\ln[L(Y|X, \omega = \{\beta, \mu\})] = \sum_{i=1}^{N} 1(Y_i = 0)\ln[-\Phi(X_i'\beta)] + \qquad \text{Eq. 10}$$
$$\sum_{j=1}^{J-1} 1(Y_i = j)\ln[\Phi(\mu_j - X_i'\beta) - \Phi(\mu_{j-1} - X_i'\beta)],$$
$$+ 1(Y_i = J)\ln[1 - \Phi(\mu_{J-1} - X_i'\beta)],$$

$$\ln[L(Y|X, \omega = \{\beta\})] = \sum_{i=1}^{N} \sum_{j=0}^{J} 1(Y_i = j)\ln[\Lambda(X_i'\beta_j)], \qquad \text{Eq. 11}$$

where 1(·) denotes an indicator function, i.e., a function which takes the value 1 if its argument is true and the value 0 if its argument is false.

An alternative method of estimating ω is the generalized method of moments, which is given by the following minimization equation:

$$w = \arg\min_{\omega} g(Y, X, \omega)' W^{-1} g(Y, X, \omega), \qquad \text{Eq. 12}$$

where g(Y, X, ω) is a vector of moment conditions, i.e., expected-value functions of the form E[f(Y, X, ω)]=0, and W is a matrix which weights the moment conditions. For example, one application of the generalized method of moments is that of nonlinear least squares for the probit model in Eq. 2, in which g(Y, X, ω) and W are defined as follows:

$$g(Y, X, \omega = \{\beta\}) = \frac{1}{N}\sum_{i=1}^{N} [Y_i - X_i'\beta] \frac{\partial \Phi(X_i'\beta)}{\partial \beta}, \; W = I, \qquad \text{Eq. 13}$$

where I denotes the identity matrix.

Additional methods of estimating ω are nonparametric and semiparametric methods, such as kernel estimation; and simulation methods, such as the method of maximum simulated likelihood and the method of simulated moments.

Except for idealized cases of the distribution function F, a probability regression model will be a nonlinear function of ω. Hence, none of the methods of estimating ω described above will yield unbiased estimates of ω, but if the model is correctly specified, the estimates of ω will be consistent. That is, the expected values of parameter estimates w are not the true values of parameters ω, and parameter estimates w attain the true values of parameters ω only as the number of observations N in the dataset approaches infinity. However, a substantially accurate estimate of ω that is useful in most applications is usually obtained long before N becomes infinite. The value of N used to obtain a substantially accurate estimate of ω is typically unique to each probability regression model. Thus, because parameter estimates w converge to parameters ω only in the limit of observations, it is productive to repeat the estimation methodology should additional observations become available, a process referred to as updating the estimates.

Most often, parameters ω will act as multiplicative constants upon the predictors X. For example, if X=[1 $X_1$ $X_2$]', w={β}=[$\beta_0$ $\beta_1$ $\beta_2$]', and F(X, ω={β})=F(X'β), then the general form of a probability regression model can be written as follows:

$$Pr(Y|X,\omega=\{\beta\})=F(\beta_0+\beta_1 X_1+\beta_2 X_2). \qquad \text{Eq. 14}$$

However, this need not be the only use of ω. As another example, elements of ω can act as a power:

$$Pr(Y|X,\omega)=F(\omega_0 X_1^{\omega_1} X_2^{\omega_2}). \qquad \text{Eq. 15}$$

As yet another example, elements of ω can be specific to a particular subject. For example, let $\beta_i$ denote a set of parameters which is unique to a particular subject, and let $\beta_i$ be described by a distribution function G. Then, Eq. 14 can be augmented by adding $\beta_i$, which defines a new distribution function F*:

$$Pr(Y|X,\omega=\{\beta\})=F^*(X,\omega=\{\beta\})=\int F(\beta_0+\beta_1 X_1+\beta_2 X_2+\beta_i) G(\beta_i)d\beta_i. \qquad \text{Eq. 16}$$

In accordance with other embodiments, ω can be used in different ways in other specifications of the probability regression model.

Embodiments of this invention can use a single probability regression model, or combinations of different probability regression models.

General Applications

In a general embodiment of the invention, the parameters ω of a probability regression model of a cardiovascular disease are estimated. In this embodiment, disease status information, clinical data, and data derived from cardiovascular sound signals are first collected from a group of subjects, which can optionally be identified by one or more common characteristics. Using an estimation methodology, parameter estimates w of the parameters ω of the probability regression model are then generated. The general methodology employed in this embodiment can be as follows.

First, disease status information for the cardiovascular disease of interest is collected from each subject in the group. Disease status information is generally any objective or subjective analysis of the subject with respect to the cardiovascular disease of interest. For example, in an embodiment, disease status information is a physician's assessment of the subject with respect to the cardiovascular disease of interest. Once disease status information is obtained, it is represented as the event of interest Y. In some cases, the disease status information can be directly represented as the event of interest Y. For example, if Y represents the survival time until an event relating to the cardiovascular disease, the relevant disease status information can contain data regarding the length of time the subject survived the event. However, some transformation of the disease status information can be used to represent it as the event of interest Y. For example, if Y is formulated as a binomial or multinomial event, then the disease status information is typically sorted into one of the categories; a categorical formulation of Y is often not inherent in the disease status information.

Second, clinical data and data derived from cardiovascular sound signals are collected from each subject in the group to form the predictors X. The clinical data can be collected from any source which contains this data, so long as the data collected are commensurate with, i.e., the same as, substantially the same as, or of similar type as, that specified by the probability regression model. For example, if the probability regression model specifies that X includes whether or not the subject smokes, a "yes/no" formulation of this data is commensurate with a "number of cigarettes smoked per day" formulation. Clearly, any positive number of cigarettes smoked per day corresponds to the "yes" response, and a zero number of cigarettes smoked per day corresponds to the "no" response. As a further example, in one embodiment, the clinical data are collected from the subject's medical record.

The data derived from cardiovascular sound signals can be collected using any system capable of generating this data, so long as the data generated are commensurate with, i.e., the same as, substantially the same as, or of similar type as, with that specified by the probability regression model. For example, if the probability regression model specifies that X includes whether or not a split S1 sound is present in the subject, a formulation in which this data is provided by a physician's auscultative assessment is commensurate with a formulation in which this information is provided by a machine. As a further example, in one embodiment, the data derived from cardiovascular sound signals are collected from the system described in U.S. Patent Application Publication No. 2003/0229289. Some transformations can be used to transform the clinical data and the data derived from cardiovascular sound signals into the predictors X. Such transformations include functional transformations and conversions of units.

Third, using the combined data on Y and X from the group of subjects, the parameters $\omega$ are estimated using an estimation methodology. For example, in one embodiment, the parameter estimates w are obtained using machine-readable code containing steps for applying the methodology. These parameter estimates w are then retained for later use.

In another general embodiment of the invention, the probability $Pr(Y|X, w)$ of the event of interest Y, which is in this embodiment the probability of a cardiovascular disease event, is generated for a new subject using previously generated parameter estimates w. Clinical data and data derived from cardiovascular sound signals are first collected for this new subject, and the previously generated parameter estimates w are retrieved. Using the predictors X and the parameter estimates w, the probability $Pr(Y|X, w)$ is then generated. This embodiment differs from the previous embodiment in that disease status information is not necessarily required to generate the probability $Pr(Y|X, w)$, whereas it is used to generate the parameter estimates w. The general methodology employed in this embodiment is as follows.

As discussed in the description of the previous general embodiment, the previously generated parameter estimates w can be generated using a group of subjects with one or more common characteristics. It is then first verified that the new subject also shares the same characteristics. If the new subject does not share these characteristics, a bias might be induced in the probability $Pr(Y|X, w)$, which is undesirable.

Second, clinical data and data derived from cardiovascular sound signals are collected from the new subject to form the predictors X. The clinical data can be collected from any source which contains this data, so long as the data collected are commensurate with, i.e., the same as, substantially the same as, or of similar type as, that specified by the probability regression model. For example, if the probability regression model specifies that X includes whether or not the subject smokes, a "yes/no" formulation of this data is commensurate with a "number of cigarettes smoked per day" formulation. Clearly, any positive number of cigarettes smoked per day corresponds to the "yes" response, and a zero number of cigarettes smoked per day corresponds to the "no" response. As a further example, in one embodiment, the clinical data are collected from the new subject's medical record.

The data derived from cardiovascular sound signals can be collected using any system capable of generating this data, so long as the data generated are commensurate with, i.e., the same as, substantially the same as, or of similar type as, that specified by the probability regression model. For example, if the probability regression model specifies that X includes whether or not a split S1 sound is present in the subject, a formulation in which this information is provided by a physician's auscultative assessment is commensurate with a formulation in which this information is provided by a machine. As a further example, in one embodiment, the data derived from cardiovascular sound signals are collected from the system described in U.S. Patent Application Publication No. 2003/0229289. Some transformations can be used to transform the clinical data and the data derived from cardiovascular sound signals into the predictors X. Such transformations include functional transformations and conversions of units.

Third, using the predictors X and the previously generated parameter estimates w, the probability regression model is evaluated to generate the probability $Pr(Y|X, w)$, which is the probability of a cardiovascular disease event Y in the new subject. For example, in one embodiment, the probability $Pr(Y|X, w)$ is generated using machine-readable code containing steps for mathematically evaluating the probability regression model.

These two general embodiments can be used independently or together. For example, the first general embodiment can be used to generate parameter estimates w of a probability regression model of cardiovascular disease, and these same parameter estimates w can then be used in the second general embodiment to generate the probability $Pr(Y|X, w)$ of a cardiovascular disease event.

Specific Applications

Based on the above general description of embodiments of the invention, more specific embodiments of the system are now described.

FIG. 1 is a block diagram of a processor system 10 that can be used to model cardiovascular disease using a probability regression model according to an embodiment of the invention. The processor system 10 can be, for example, a commercially available personal computer, a workstation, or a less complex computing or processing device that is dedicated to performing one or more specific tasks. For example, the processor system 10 can be a dedicated network communication terminal, client, or server. Additionally, or alternatively, the processor system 10 can be included as a part of a medical diagnostic device used to obtain information regarding a subject.

The processor system 10 includes a processor 12, which according to one or more embodiments of the invention can be a commercially available microprocessor, such as the 80X86 series of microprocessors available from Intel Corp., the Power PC series of microprocessors available from Motorola, Inc., the AMD series of microprocessors available from Advanced Micro Devices, Inc., or other similar microprocessors. Alternatively, the processor 12 can be an application-specific integrated circuit (ASIC), which is designed to achieve one or more specific functions, or enable one or more specific devices or applications. For example, the processor can be an ASIC designed to process medical or diagnostic information, calculate probabilities or perform other mathematical calculations, and so forth.

Alternatively, the processor 12 can optionally include one or more individual sub-processors or coprocessors. For example, the processor can include a graphics coprocessor that is capable of rendering graphics, an encryption/decryption coprocessor, a coder/decoder (CODEC) communications processor, a database query processor, a controller that is capable of controlling one or more external or peripheral devices, a sensor that is capable of receiving sensory input from one or more sensing devices, and so forth.

The processor system 10 can also include a memory component 14. As shown in FIG. 1, the memory component 14 can include one or more types of memory. For example, the memory component 14 can include a read only memory (ROM) component 14a and a random access memory (RAM) component 14b. The memory component 14 can also include other types of memory not illustrated in FIG. 1 that are suitable for storing data in a form retrievable by the processor 12, or by other devices (e.g., devices connected to the processor system via the network 50). For example, electronically programmable read only memory (EPROM), erasable electrically programmable read only memory (EEPROM), flash memory, as well as other suitable forms of memory can be included as part of the memory component 14.

The processor system 10 can also include a storage component 16, which is configured to store data in one or more predetermined formats. According to one or more embodiments of the invention, the storage component 16 can be a longer-term storage device than the memory component 14. For example, according to one or more embodiments of the invention, the storage component 16 can be a database configured to store data in one or more formats, such as a SQL format, a Database 2 (DB2) format, an Extensible Markup Language (XML) format, an Oracle database format (e.g., Oracle 8i, Oracle 9i, Oracle 11i, etc.), or other desired database formats. Additionally, the storage component 16 can include one or more standard storage components, such as a disk drive, a compact (CD) drive, a digital video disk (DVD) drive, a flash memory drive, or the like.

The various components of the processor system 10 can communicate via a bus 18, which is connected to each of the components of the processor system 10, and allows data to be transferred between the various components. The bus 18 can use any data transfer protocol suitable for communicating data between the various components of the processor system 10. The protocol used by the bus 18 can include any suitable bus protocol, such as Peripheral Component Interconnect (PCI), Industrial Standard Architecture (ISA), Extended ISA (EISA), Accelerated Graphics Port (AGP), Micro Channel, VESA Local Bus (VL-bus), NuBus, TURBOchannel, VersaModule Eurocard Bus (VMEbus), MULTIBUS, Subscriber Trunk Dialing (STD) bus, and other suitable bus protocols. For example, by way of the bus 18, the processor 12 communicates with the memory component 14 and the storage component 16, and can store data in or retrieve data previously stored in the memory component 14 or storage component 16.

Additionally, components of the processor system 10 can communicate with devices that are external to the processor system 10 by way of an input/output (I/O) component 20, which is also connected to the bus 18. According to one or more embodiments of the invention, the I/O component 20 can include a variety of suitable communication interfaces. For example, the I/O component 20 can include wired connections, such as standard serial ports, parallel ports, universal serial bus (USB) ports, S-video ports, large area network (LAN) ports, small computer system interface (SCSI) ports, and so forth. Additionally, the I/O component 20 can include, for example, wireless connections, such as infrared ports, optical ports, Bluetooth wireless ports, wireless LAN ports, wireless fidelity (Wi-Fi) wireless ports, ultra-wide band (UWB) wireless ports, or the like.

By way of the I/O component 20 the processor system 10 can communicate with other local devices, such as peripheral devices 30, which can include any of a number of devices desirable to be accessed by or used in conjunction with the processor system 10. For example, the peripheral devices 30 with which the processor system 10 can communicate via the I/O component 20, can include a processor, a memory component, a storage component, a printer, a scanner, a storage component (e.g., an external disk drive, database, etc.), or any other device that a user desires to connect to the processor system 10.

The processor system 10 can also be connected to a network 50 via the I/O component 20. The network 50 can include one or more of a variety of communications networks. For example, according to one or more embodiments of the invention, the network can include the Internet. Additionally, or alternatively, the network 50 can include a variety of other communications networks, including, for example, a LAN, a wide area network (WAN), a virtual LAN (VLAN), or other suitable network.

It should be understood that the processor system 10 can also include a variety of other components not shown in FIG. 1, depending upon the desired functionality of the processor system 10. Additionally, it should be understood that other processor systems 10a and 10b having similar or different configurations to the processor system 10 can be connected to the network 50. Indeed, many more processor systems 10 than those shown in FIG. 1 can be interconnected via one or more networks 50. Any of the processor systems 10, 10a, 10b can, therefore, communicate with one another, or with peripheral devices 30 connected to one or more of the multiple processor systems 10, via the network 150.

Figure 2:
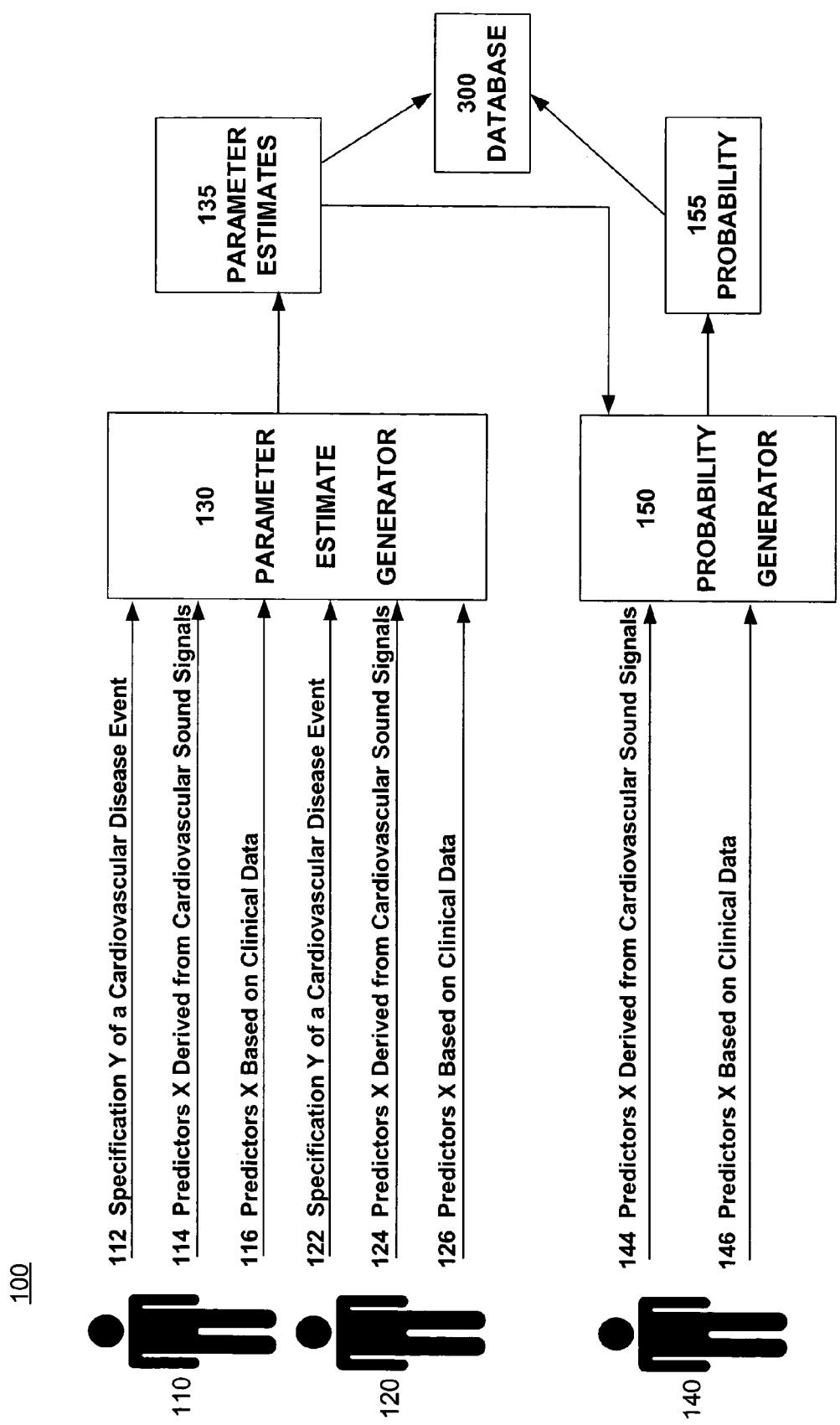
FIG. 2 illustrates a system for generating a parameter estimate of a probability regression model of cardiovascular disease, and for predicting a cardiovascular disease event using a probability generated from previously generated parameter estimates, according to an embodiment of the invention.

FIG. 2 illustrates a system 100 for generating parameter estimates of a probability regression model of cardiovascular disease, and for predicting a cardiovascular disease event using a probability generated from previously generated parameter estimates, according to an embodiment of the invention. It should be understood that the system 100 shown in FIG. 2 can form part of one or more processor systems 10, and that the various components of the system 100 can be facilitated by one or more processor systems 10 and the respective components of those processor systems 10.

For purposes of generating parameter estimates of a probability regression model for cardiovascular disease, system 100 performs as follows. First, specifications Y 112 and 122 of a cardiovascular disease event based on disease status information, predictors X 114 and 124 derived from cardiovascular sound signals, and predictors X 116 and 126 based on clinical data are received from several subjects 110 and 120, respectively. Subjects 110 and 120 when considered together should be interpreted as some indefinite number of subjects, and not necessarily as exactly two subjects. Next, the specifications Y 112 and 122 of a cardiovascular disease event based on disease status information, the predictors X 114 and 124 derived from cardiovascular sound signals, and the predictors X 116 and 126 based on clinical data are passed to a parameter estimate generator 130 for generation of parameter estimates 135 (i.e., w) of the probability regression model. These parameter estimates w 135 can, for example, be stored in a database 300.

For purposes of predicting a cardiovascular disease event using a probability generated from previously generated parameter estimates, system 100 performs as follows. First, predictors X 144 derived from cardiovascular sound signals and predictors X 146 based on clinical data are received from a new subject 140. The predictors X 144 derived from cardiovascular sound signals and the predictors X 146 based on clinical data are commensurate with, i.e., the same as, substantially the same as, or of similar type as, the predictors X 114 and 124 derived from cardiovascular sound signals and the predictors X 116 and 126 based on clinical data, respectively, associated with the several subjects 110 and 120, which were used to obtain parameter estimates w 135. Next, the predictors X 144 derived from cardiovascular sound signals and the predictors X 146 based on clinical data associated with the new subject, and the previously generated parameter estimates w 135 are passed to a probability generator 150 for generation of a probability 155 (e.g., Pr(Y|X, w)) of a cardiovascular disease event. The probability 155 of a cardiovascular disease event can, for example, be stored in a database 300.

The various components of system 100 can be implemented on one or more computers, preprogrammed chips, or other programmable devices. Examples of such implementations are given below. These are purely examples of the invention and should not be considered limiting.

As one general example, all components of system 100 can be implemented on a single programmable device (e.g., the processor system 10 of FIG. 1) in which all data and instructions are held in a machine-readable memory. The following are more specific examples of this general example.

EXAMPLE 1

System 100 can be implemented on a single standalone, offline computer (e.g., the processor system 10 shown in FIG. 1) accessible by one or more operators. Certain functions of this computer can be accessible to some of the operators but not to others, depending upon the access control settings for the computer. The memory used in this computer (e.g., the memory component 14 or storage device 16 shown in FIG. 1) can be one or more of a variety of memory types, e.g., magnetic or optical storage devices, flash memory, EPROMS, RAID devices, or other devices suitable for storing one or more flat-files, SQL files, or other databases (e.g., the storage device 16 shown in FIG. 1) residing on the computer in which specifications Y 112 and 122 of a cardiovascular disease event, predictors X 114 and 124 derived from cardiovascular sound signals, predictors X 116 and 126 based on clinical data, predictors X 144 derived from cardiovascular sound signals, and predictors X 146 based on clinical data are stored. Such databases stored in memory can be populated by one or more of the operators manually entering these data into the databases. These data can be transmitted to the operators from one or more physicians, cardiovascular diagnosticians, or other agents using paper records delivered through the post or similar mode, paper records delivered by facsimile, electronic records delivered over the Internet, or telephone conversations.

Parameter estimate generator 130 and probability generator 150 can be implemented using any suitable instructions, such as C, C++, Java, FORTRAN, COBOL, Matlab, or other programming instructions, residing on this computer, each of which can be executed at the discretion of an operator or in a batch mode. For example, parameter estimate generator 130 can initially be run manually by the operators to obtain parameter estimates w 135, and then configured to automatically attempt to update parameter estimates w 135 any time additional data from one or more new subjects 140 are received.

The memory can also be used to store parameter estimates w 135 for one or more probability regression models of cardiovascular disease or one or more probabilities Pr(Y|X, w) 155 of a cardiovascular disease event, in which case parameter estimates w 135 and probabilities Pr(Y|X, w) 155 of a cardiovascular disease event can be manually entered into the databases by the operators or automatically entered into the databases as part of the instructions executed by parameter estimate generator 130 and probability generator 150.

The probability Pr(Y|X, w) 155 of a cardiovascular disease event can be transmitted by the operators to one or more physicians, cardiovascular diagnosticians, or other agents, such as those who originally sent the data, using a paper record delivered through the post or similar mode, a paper record delivered by facsimile, an electronic record delivered over a network (e.g., the Internet), or a telephone conversation.

EXAMPLE 2

System 100 can be implemented on a single networked, online computer (e.g., the processor system 10 shown in FIG. 1) accessible by one or more operators and by one or more physicians, cardiovascular diagnosticians, or other agents. (As will be discussed in later examples, such a system can be extended to allow for distribution of its various computing functions, storage capabilities, or other functions amongst multiple computers.) For example, system 100 can be a publicly-accessible, semi-publicly-accessible, or privately-accessible computer, accessible via one or more HTTP servers, HTTPS servers, FTP servers, SFTP servers, telnet servers, SSH servers, SQL servers, or similar devices, which permit communication with the computer over a network (e.g., the network 50 shown in FIG. 1). Certain functions of this computer can be accessible to some of the operators, physicians, cardiovascular diagnosticians, and other agents, but not to others depending upon the access control settings for the device or network by which it is accessed.

The memory used in system 100 can be suitable for storing one or more flat-files, SQL files, or other databases residing on the computer or processor device, in which specifications Y 112 and 122 of a cardiovascular disease event, predictors X 114 and 124 derived from cardiovascular sound signals, predictors X 116 and 126 based on clinical data, predictors X 144 derived from cardiovascular sound signals, and predictors X 146 based on clinical data are stored.

These data can be transmitted to the server by the physicians, cardiovascular diagnosticians, and other agents by means of one or more suitable interfaces, such as HTTP, FTP, SFTP, telnet, SSH, or CGI, and can be transmitted in one or more suitable formats, such as HTML or SQL. These data can be entered directly into the database by means of the client interfaces.

Parameter estimate generator 130 and probability generator 150 can be implemented using any suitable instructions, such as Java, JavaScript, Perl, PHP, HTML/CGI, or other instructions, residing on the server, each of which can be executed at the discretion of an operator, physician, cardiovascular diagnostician, or other agent, or in a batch mode. For example, parameter estimate generator 130 and probability generator 150 can be configured to automatically execute the instructions for one or more of the parameter generation task, the probability generation task, and the optional updating of the parameter estimates task when data is received from the client interfaces. The memory can also be used to store parameter estimates w 135 of one or more probability regression models of cardiovascular disease or one or more probabilities Pr(Y|X, w) 155 of a cardiovascular disease event, in which case parameter estimates w 135 and probabilities Pr(Y|X, w) 155 of a cardiovascular event can be automatically entered into the databases as part of the instructions executed by parameter estimate generator 130 and probability generator 150. The probability Pr(Y|X, w) 155 of a cardiovascular disease event can be transmitted to one or more physicians, cardiovascular diagnosticians, or other agents, such as those who originally sent the data, using one or more of the client interfaces.

EXAMPLE 3

Referring to Example 1 and Example 2, various functions of the systems described in those examples can be combined into a mixed offline/online system. For example, the transmission of specifications Y 112 and 122 of a cardiovascular disease event, predictors X 114 and 124 derived from cardiovascular sound signals, predictors X 116 and 126 based on clinical data, predictors X 144 derived from cardiovascular sound signals, and predictors X 146 can be implemented using those components in the online system in Example 2, and parameter estimate generator 130 and probability generator 150 can be implemented using those components in the offline system in Example 1. As another example, probability Pr(Y|X, w) 155 of a cardiovascular disease event generated by the system in Example 2 can be transmitted to one or more physicians, cardiovascular diagnosticians, or other agents, such as those who originally sent the data, using a paper record delivered through the post or similar mode, a paper record delivered by facsimile, an electronic record delivered over the Internet, or a telephone conversation, as in Example 1.

EXAMPLE 4

Referring to Example 2, specifications Y 112 and 122 of cardiovascular disease event, predictors X 114 and 124 derived from cardiovascular sound signals, predictors X 116 and 126 based on clinical data, predictors X 144 derived from cardiovascular sound signals, and predictors X 146 based on clinical data can be collected by a technician operating a cardiovascular diagnostic machine, and this cardiovascular diagnostic machine can have embedded in it one or more client interfaces with which to communicate with the computer. The computer can transmit probability Pr(Y|X, w) 155 of a cardiovascular disease event back to the cardiovascular diagnostic machine using the one or more embedded clients, or to a physician, cardiovascular diagnostician, or other agent using the above-mentioned methods.

As another general example, components of system 100 can be implemented on several programmable devices in which the data and instructions are held in one or more machine-readable memories. The following are more specific examples of this general example.

EXAMPLE 5

Referring to Example 1, the memory and instructions residing on the computer described in that example can be synchronized, mirrored, copied, or otherwise duplicated across several standalone computers. For example, this can be done to permit access to the functions present in that computer to several operators who can not be in the same physical location. As another example, this can be done to allow for fault-tolerance in the functions present in the single standalone computer.

EXAMPLE 6

Referring to Example 2, the memory and instructions residing on the computer described in that example can be synchronized, mirrored, copied, or otherwise duplicated across several standalone computers. For example, this can be done to allow for load-balancing or fault-tolerance in the functions present in the single networked computer.

EXAMPLE 7

Referring to Example 1, various components of the computer described in that example can be implemented across one or more standalone computers. For example, there can be one computer upon which the instructions for parameter estimate generator 130 reside, and a different computer upon which the instructions for probability generator 150 reside, each of which contains a copy of the memory. As another example, there can be one computer upon which the instructions for parameter estimate generator 130 and probability generator 150 reside, and another computer which contains instructions for transmitting the probability Pr(Y|X, w) 155 of a cardiovascular disease event.

EXAMPLE 8

Referring to Example 2, various components of the computer described in that example can be implemented across one or more networked computers (e.g., the processor systems 10, 10a, and 10b of FIG. 1). For example, there can be one computer containing the memory, another computer containing the instructions for parameter estimate generator 130, and another computer containing the instructions for probability generator 150. These latter two computers can communicate with the former in order to access the memory. As another example, there can be one computer containing the client interfaces and the memory, and another computer containing a copy of the memory that is synchronized over a network as well as instructions for parameter estimate generator 130 and probability generator 150.

Figure 3:
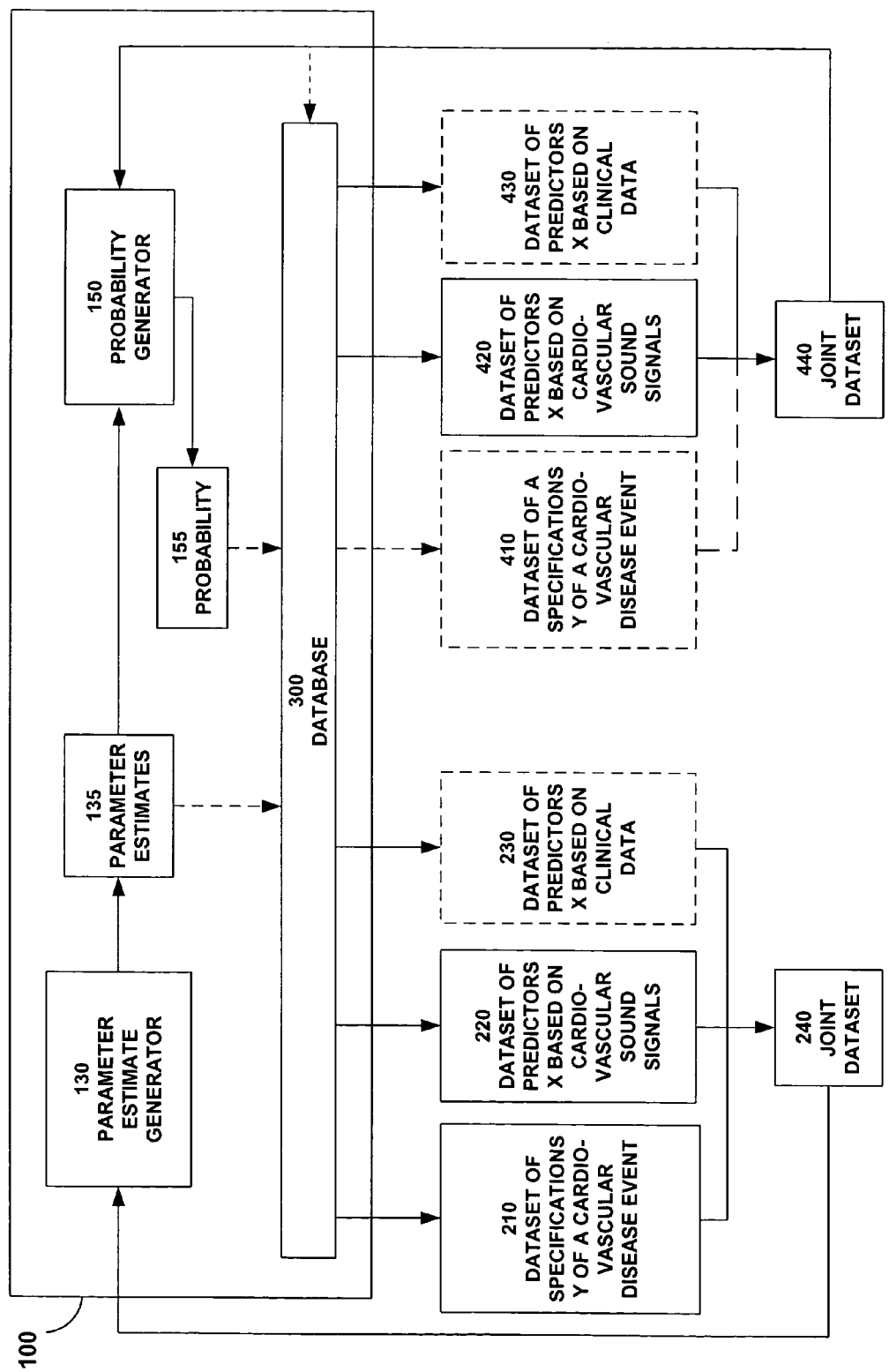
FIG. 3 is a block diagram illustrating a methodology of the system illustrated in FIG. 2.

FIG. 3 is a block diagram illustrating a methodology of the system 100 illustrated in FIG. 2. FIG. 3 illustrates in greater detail how parameter estimates w 135 and probability Pr(Y|X, w) 155 of a cardiovascular disease event illustrated in FIG. 2 can be generated in accordance with an embodiment of the invention. Several components of the methodology illustrated in FIG. 1 are shown as optional with dashed lines, and can be either omitted or included depending upon the specific funtionality desired. For purposes of generating parameter estimates w 135 of a probability regression model of cardiovascular disease, the system 100 illustrated in FIG. 3 performs as follows. First, a joint dataset 240 of data from several subjects 110 and 120 (shown in FIG. 2) is constructed from a dataset 210 of specifications Y 112 and 122 (shown in FIG. 2) of a cardiovascular disease event based on disease status information, a dataset 220 of predictors X 114 and 124 (shown in FIG. 2) derived from cardiovascular sound signals, and an optional dataset 230 of predictors X 116 and 126 (shown in FIG. 2) based on clinical data.

Figure 4:
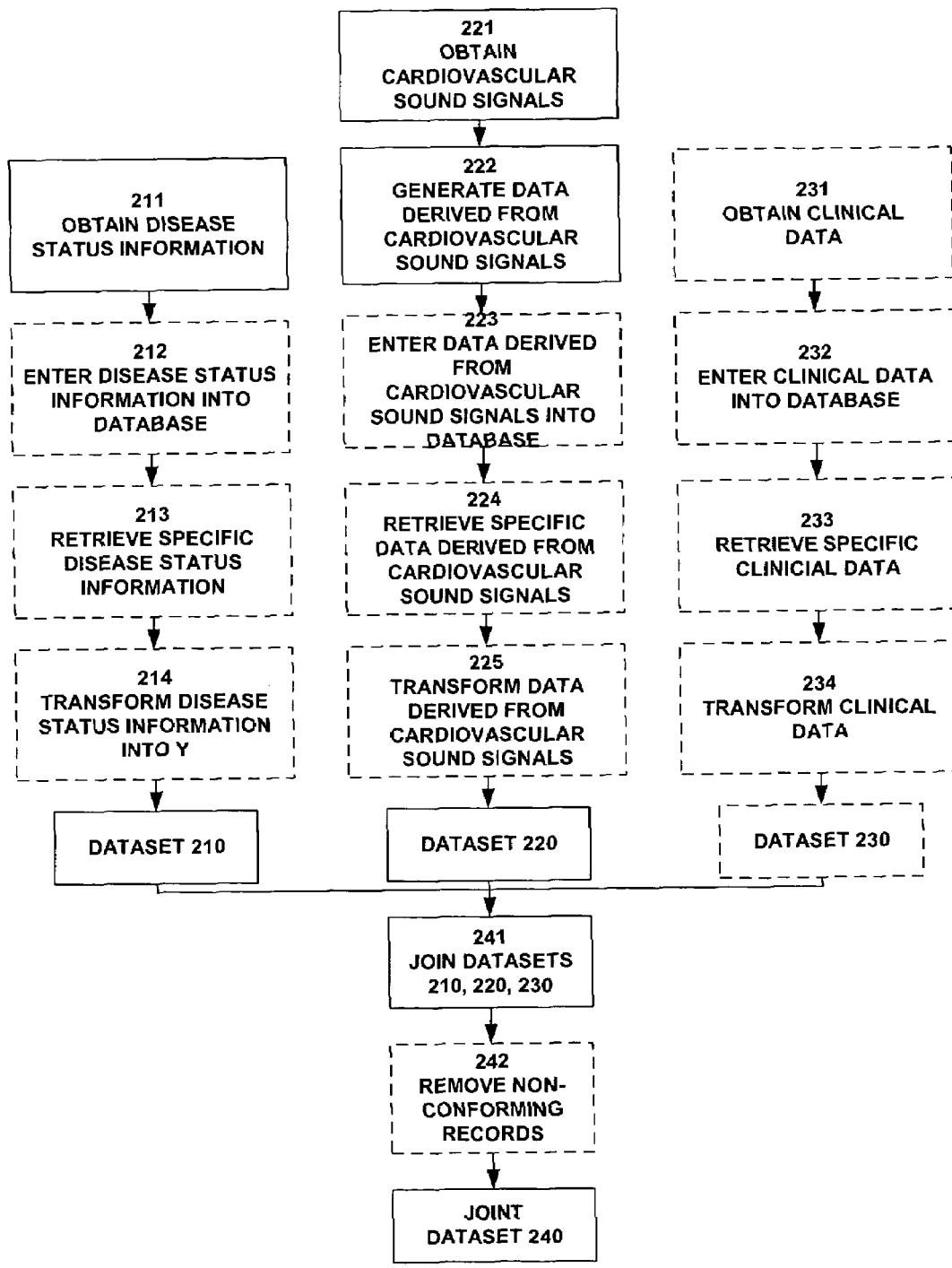
FIG. 4 is a flowchart illustrating steps for generating a dataset to be used in generating a parameter estimate of a probability regression model of cardiovascular disease in the system of FIG. 2 or FIG. 3.

FIG. 4 is a flowchart illustrating steps for generating a joint dataset 240, which can be used to generate parameter estimates w 135 of a probability regression model of cardiovascular disease in the system of FIG. 2 or FIG. 3. Several steps shown in FIG. 4 are shown as optional with dashed lines, and can be either omitted or included depending upon the specific functionality desired.

Steps for generating dataset 210 of specifications Y 112 and 122 of a cardiovascular disease event based on disease status information are illustrated in FIG. 4. The disease status information for the subjects 110 and 120 is obtained in step 211. In an optional step 212, the disease status information for each of the several subjects 110 and 120 is entered as a record into a database 300 (shown in FIG. 3). In an optional step 213, the records of disease status information to be used in the probability regression model are retrieved from database 300. In an optional step 214, any transformations of the retrieved records of disease status information used to transform these data into specifications Y 112 and 122 of a cardiovascular disease event are applied. The dataset 210 is then complete.

Steps for generating dataset 220 of predictors X 114 and 124 derived from cardiovascular sound signals are also illustrated in FIG. 4. In a step 221, cardiovascular sound signals are obtained from each of the several subjects 110 and 120. In a step 222, data derived from cardiovascular sound signals are generated from the cardiovascular sound signals of each of the several subjects 110 and 120. In an optional step 223, data derived from cardiovascular sound signals for each of the several subjects 110 and 120 are entered a record into database 300. In an optional step 224, the records of data derived from cardiovascular sound signals to be used in the probability regression model are retrieved from database 300. In an optional step 225, any transformations of the retrieved records of data derived from cardiovascular sound signals used to transform these data into predictors X 114 and 124 derived from cardiovascular sound signals are applied. The dataset 220 is then complete.

Steps for generating dataset 230 of predictors X 116 and 126 based on clinical data are also illustrated in FIG. 4. In step 231, clinical data for one or more subjects 110 and 120 are obtained. In an optional step 232, clinical data for each of the several subjects 110 and 120 are entered as a record into database 300. In an optional step 233, the records of clinical data to be used in the probability regression model are retrieved from database 300. In an optional step 234, any transformations of the retrieved records of clinical data used to transform these data into predictors X 116 and 126 based on clinical data are applied. The dataset 230 is then complete.

Steps for constructing joint dataset 240 composed of dataset 210 of specifications Y 112 and 122 of a cardiovascular disease event based on disease status information, dataset 220 of predictors X 114 and 124 derived from cardiovascular sound signals, and dataset 230 of predictors X 116 and 126 based on clinical data are also illustrated in FIG. 4. In a step 241, datasets 210, 220, and 230 are joined. In an optional step 242, any records in the joint dataset that do not satisfy common characteristics specified by the probability regression model can be removed from the joint dataset. The joint dataset 240 is then complete.

Referring again to FIG. 2, once joint dataset 240 is complete, the probability regression model is estimated by parameter estimate generator 130 using machine-readable code, e.g., as implemented on a processor-based device, such as the processor device 10 (shown in FIG. 1). The input to probability estimate generator 130 is joint dataset 240, and the output of parameter estimate generator 130 is parameter estimates w 135, which can be optionally stored in a database 300.

Figure 5:
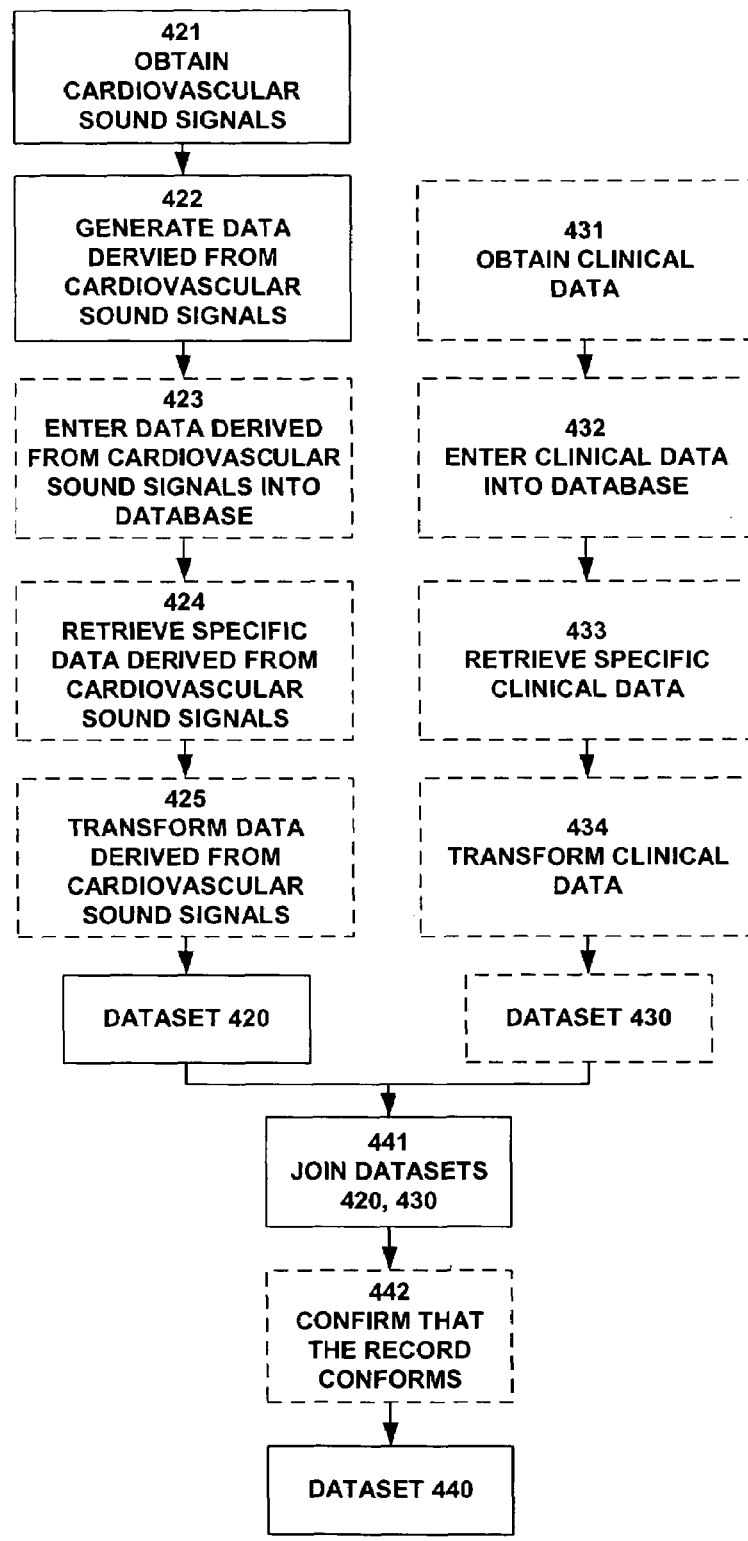
FIG. 5 is a flowchart illustrating steps for generating a dataset to be used in generating a probability of a cardiovascular disease event using a probability regression model in the system of FIG. 2 or FIG. 3.

For purposes of predicting a cardiovascular disease event using a probability generated from previously generated parameter estimates w 135, the system 100 illustrated in FIG. 3 performs as follows. First, a joint dataset 440 using data from new subject 140 (shown in FIG. 2) is constructed from a dataset 420 of predictors X 144 (shown in FIG. 2) derived from cardiovascular sound signals and an optional dataset 430 (shown in FIG. 2) of predictors X 146 based on clinical data. FIG. 5 is a flowchart illustrating steps for generating joint dataset 440, which can be used to generate a probability Pr(Y|X, w) 155 of a cardiovascular disease event in the system of FIG. 2 or FIG. 3. Several steps shown in FIG. 5 are shown as optional with dashed lines, and can be either omitted or included depending upon the specific functionality desired.

Steps for generating dataset 420 of predictors X 144 derived from cardiovascular sound signals are illustrated in FIG. 5. In a step 421, cardiovascular sound signals are obtained from new subject 140. In a step 422, data derived from cardiovascular sound signals are generated from cardiovascular sound signals of new subject 140. In an optional step 423, data derived from cardiovascular sound signals for the new subject are entered as a record into database 300 (shown in FIG. 3). In an optional step 424, the record of data derived from cardiovascular sound signals to be used in the probability regression model is retrieved from database 300. In an optional step 425, any transformations of the retrieved record of data derived from cardiovascular sound signals that are used to transform these data into predictors X 144 derived from cardiovascular sound signals are applied. The dataset 420 is then complete.

Steps for generating dataset 430 of predictors X 146 based on clinical data are also illustrated in FIG. 5. Clinical data for the new subject 140 are obtained in step 431. In an optional step 432, clinical data for new subject 140 are entered as a record into database 300. In an optional step 433, the record of clinical data to be used in the probability regression model is retrieved from database 300. In an optional step 434, any transformations of the retrieved record of clinical data used to transform these data into predictors X 146 based on clinical data are applied. The dataset 430 is then complete.

Steps for constructing joint dataset 440 composed of dataset 420 of predictors X 144 derived from cardiovascular sound signals and dataset 430 of predictors X 146 based on clinical data are also illustrated in FIG. 5. In a step 441, datasets 420 and 430 are joined. In an optional step 442, the record in the joint dataset is examined to ensure that any common characteristics specified by of the probability regression are satisfied. The joint dataset 440 is then complete.

Referring again to FIG. 3, once joint dataset 440 is complete, probability Pr(Y|X, w) 155 of a cardiovascular disease event is generated by probability generator 150 using machine-readable code, e.g., as implemented on a processor-based device, such as the processor device 10 (shown in FIG. 1). The inputs to probability generator 150 are previously generated parameter estimates w 135 and joint dataset 440, and the output of probability generator 150 is the probability Pr(Y|X, w) 155 of a cardiovascular disease event, which can be optionally stored in a database 300.

Assuming that a dataset 410 of a specification Y of a cardiovascular disease event as described below can be generated for new subject 140, the system 100 illustrated in FIG. 3 performs as follows to update the parameter estimates w 135. First, a dataset 410 of a specification Y of a cardiovascular disease event based on disease status information is generated for new subject 140 according to steps 211-214 (shown in FIG. 4). Dataset 410 is optionally stored in database 300.

Dataset 410 of a specification Y of a cardiovascular disease event based on disease status information, dataset 420 of predictors X 144 derived from cardiovascular sound signals, and dataset 430 of predictors X 146 based on clinical data are appended to dataset 210 of specifications Y 112 and 122 of a cardiovascular disease event based on disease status information, dataset 220 of predictors X 114 and 124 derived from cardiovascular sound signals, and dataset 230 of predictors X 116 and 126 based on clinical data, respectively.

Assuming that the new subject satisfies common characteristics specified by the probability regression model, a new joint dataset 240 can be generated by reapplying the methodology used to generate the original joint dataset 240. This new joint dataset 240 has an additional observation relative to the original joint dataset 240. Updated parameter estimates w 135 can be generated by reapplying the methodology used to generate the original parameter estimates w 135, using the new joint dataset 240 as input. Updating of parameter estimates w 135 can be performed each time a new subject 140 is available.

SPECIFIC EXAMPLES OF EMBODIMENTS OF THE INVENTION

Based on the above description of system 100 (shown in FIG. 2 and FIG. 3), four specific examples (Example I shown in FIGS. 13-14, Example II shown in FIGS. 15-16, Example III shown in FIGS. 17-18, and Example IV shown in FIGS. 19-20) of embodiments of that system 100 are now described. These embodiments are purely examples of the invention and should not be considered limiting. Example datasets (Dataset A shown in FIGS. 6-9 and Dataset B shown in FIGS. 10-11) are used for various examples below. FIG. 12 provides descriptions of the variables used in Dataset A and Dataset B. It should be appreciated that one or more processor devices 10 (shown in FIG. 1) can be used to perform the calculations and/or data manipulation associated with the various examples discussed below.

More particularly, FIGS. 6-9 provide an example Dataset A that can be used to generate a parameter estimate of a probability regression model of cardiovascular disease. Dataset A contains disease status information, data derived from cardiovascular sound signals, and clinical data collected from 40 subjects. FIGS. 10-11 provide an example Dataset B that can be used to generate a probability of cardiovascular disease using a probability regression model of cardiovascular disease, and also to optionally update a parameter estimate of a probability regression model of cardiovascular disease. Dataset B contains data derived from cardiovascular sound signals and clinical data collected from 10 new subjects, as well as optional disease status information. FIG. 12 provides more detailed descriptions for variables in Dataset A and Dataset B.

In Dataset A, variables (2)-(6) (shown in FIG. 6), which correspond to the data entered into database 300 according to step 212, represent disease status information that was collected according to step 211 from a physician's assessment of each of the several subjects 110 and 120, who are in this dataset uniquely identified using variable (1), i.e., by ID numbers 1-40. Cardiovascular sound signals were obtained from each of the several subjects 110 and 120 according to step 221 using the system described in U.S. Patent Application Publication No. 2003/0229289; variables (7)-(24) (shown in FIG. 7 and FIG. 8), which correspond to the data entered into database 300 according to step 223, represent data derived from cardiovascular sound signals that were generated using this system for each of the several subjects 110 and 120 according to step 222. Variables (25)-(28) (shown in FIG. 9), which correspond to the data entered into database 300 according to step 232, represent clinical data collected according to step 231 from the medical record of each of the several subjects 110 and 120.

In Dataset B, variables (2)-(6) (shown in FIG. 10A), which correspond to the data entered into database 300 according to step 212, represent disease status information that was optionally collected according to step 211 from a physician's assessment of each of the new subjects 140, who are in this dataset uniquely identified using variable (1), i.e., by ID numbers 41-50. Recall that this disease status information is not necessarily required to generate a probability $Pr(Y|X, w)$ 155 of a cardiovascular disease event, but it is used to update parameter estimates w 135. Cardiovascular sound signals were obtained from each of the new subjects 140 according to step 421 using the system described in U.S. Patent Application Publication No. 2003/0229289; variables (7)-(24) (shown in FIG. 10B and FIG. 11A), which correspond to the data entered into database 300 according to step 423, represent data derived from cardiovascular sound signals that were generated using this system for each of the new subjects 140 according to step 422. Variables (25)-(28) (shown in FIG. 11B), which correspond to the data entered into database 300 according to step 432, represent clinical data that were collected according to step 231 from the medical record of each of the new subjects 140. As discussed above, the variables used in Dataset A and Dataset B are described in greater detail in FIG. 12. It will be appreciated that additional variables can be used according to one or more embodiments of the invention, and that the variables used in Dataset A and Dataset B, as described in FIG. 12, are merely example variables used for the Examples I-IV below.

EXAMPLE I

A Logit Model of Hypertension

FIGS. 13-14 provide examples of parameter estimates, probabilities, and updated parameter estimates for a logit model of hypertension, according to an embodiment of the invention illustrated by an Example I. The event of interest Y in this probability regression model is formulated as a binomial event:

$$Y = \begin{cases} 0 & \text{if hypertension is not present} \\ 1 & \text{if hypertension is present} \end{cases}.$$

Referring to the multinomial logit model in Eq. 5, the logit model shown below is a special case of that model which is constructed by setting J=1. After applying the normalizations discussed in the multinomial logit model, the functional form of the logit model is as follows:

$$Pr(Y=1|X,\omega=\{\beta\})=\Lambda(X'\beta). \qquad \text{Eq. 17}$$

(The subscripts on parameters β have been omitted because there is effectively only one set of parameters $\beta_i$ in this special case, i.e., $\beta=\beta_1$.) The probability regression model in Example I is a specific case of the probability regression model in Eq. 14.

Referring to Example I, this embodiment of system 100 performs as follows to generate parameter estimates w 135 (shown in FIG. 13) of the probability regression model specified in that example. The disease status information retrieved according to step 213 is variables (5) and (6) of Dataset A, the systolic and diastolic blood pressure. These variables can be transformed into specifications Y 112 and 122 of a cardiovascular disease event, which is in this example the existence of hypertension, according to step 214 using the following transformation:

$$Y = \begin{cases} 0 & \text{if } BP\_SYST \leq 160 \text{ and } BP\_DIAS \leq 80 \\ 1 & \text{if } BP\_SYST > 160 \text{ or } BP\_DIAS > 80 \end{cases}.$$

These transformed data from dataset 210 of specifications Y 112 and 122 of the existence of hypertension.

The data derived from cardiovascular sound signals retrieved from database 300 according to step 224 are variables (7)-(9), (16)-(18), (19)-(21), and (22)-(24) of Dataset A. These represent the number of beats recorded at each recording location, the number of S4 sounds recorded at each recording location, the heart rate recorded at each recording location, and the heart rate standard deviation recorded at each recording location. According to step 225, the following transformations of these variables can be used to transform them into predictors X 114 and 124 derived from cardiovascular sound signals:

$$AVGS4 = \frac{1}{3}\left(\frac{S4\_R}{BEATS\_R} + \frac{S4\_C}{BEATS\_C} + \frac{S4\_L}{BEATS\_L}\right),$$

$$AVGHR = \frac{1}{3}(HR\_R + HR\_C + HR\_L),$$

$$AVGHRSD = \frac{1}{3}(HRSD\_R + HRSD\_C + HRSD\_L).$$

These transformed data form dataset 220 of predictors X 114 and 124 derived from cardiovascular sound signals.

The clinical data retrieved from database 300 according to step 233 are variable (26) of Dataset A, the age. There are no transformations of clinical data according to step 234 needed to transform this variable into dataset 230 of predictors X 116 and 126 based on clinical data.

Datasets 210, 220, and 230 are then joined according to step 241. Because this probability regression model applies specifically to males, those records corresponding to those of subjects 110 and 120 who are female are removed according to step 242; because 21 out of 40 subjects in Dataset A are female, this implies that N=19. The outcome of this last step is joint dataset 240. Joint dataset 240 is then used as input to parameter estimate generator 130 for generation of parameter estimates w 135 using machine-readable code for maximum-likelihood estimation of a logit model. Referring to the maximum-likelihood equation in Eq. 7, the log-likelihood function corresponding to the logit model in Eq. 17 is as follows:

$$\ln[L(Y|X, \omega = \{\beta\})] = \qquad \text{Eq. 18}$$

$$\sum_{i=1}^{N} 1(Y_i = 1)\ln[\Phi(X_i'\beta)] + 1(Y_i = 0)\ln[1 - \Phi(X_i'\beta)].$$

Again referring to Example I, this embodiment of system 100 performs as follows to generate a probability Pr(Y|X, w) 155 (shown in FIG. 14) of the existence of hypertension, using the probability regression model specified in that example. The data derived from cardiovascular sound signals retrieved from database 300 according to step 424 are variables (7)-(9), (16)-(18), (19)-(21), and (22)-(24) of Dataset B. These represent the number of beats recorded at each recording location, the number of S4 sounds recorded at each recording location, the heart rate recorded at each recording location, and the heart rate standard deviation recorded at each recording location. According to step 425, the following transformations of these variables can be used to transform them into predictors X 144 derived from cardiovascular sound signals:

$$AVGS4 = \frac{1}{3}\left(\frac{S4\_R}{BEATS\_R} + \frac{S4\_C}{BEATS\_C} + \frac{S4\_L}{BEATS\_L}\right),$$

$$AVGHR = \frac{1}{3}(HR\_R + HR\_C + HR\_L),$$

$$AVGHRSD = \frac{1}{3}(HRSD\_R + HRSD\_C + HRSD\_L).$$

These transformed data form dataset 420 of predictors X 144 derived from cardiovascular sound signals.

The clinical data retrieved from database 300 according to step 433 are variable (26) of Dataset B, the age. There are no transformations of clinical data according to step 434 needed to transform this variable into dataset 430 of predictors X 146 based on clinical data.

Datasets 420 and 430 are then joined according to step 441. Because this model applies specifically to males, the record is examined according to step 442 to ensure that the new subject 140 is male; the probability Pr(Y|X, w) 155 is not generated for a new subject 140 who is female. The result of this last step is joint dataset 440. This joint dataset 440 and the previously generated parameter estimates w 135 are then used as inputs to probability generator 150 for generation of probability Pr(Y|X, w) 155 of the existence of hypertension using machine-readable code for mathematically evaluating a logit model. The task described in this paragraph is performed for each new subject 140 in Dataset B. Because 3 out of 10 new subjects 140 in Dataset B are male, probabilities Pr(Y|X, w) 155 are generated for only those 3 subjects.

Again referring to Example I, this embodiment of system 100 performs as follows to update parameter estimates w 135 (shown in FIG. 14) of the probability regression model specified in that example. This task can be performed because optional disease status information was indeed collected from each of the new subjects 140 in Dataset B. The disease status information for each of the new subjects 140 is variables (5) and (6) of Dataset B, the systolic and diastolic blood pressure, which is entered into database 300 according to step 212.

The procedure described above for generating joint dataset 240 can then be applied to generate a new joint dataset 240 which contains records of subjects from Dataset B in addition to records of subjects from Dataset A. Because 3 out of 10 new subjects 140 in Dataset B are male, this implies that N=22 in new joint dataset 240. Updated parameter estimates w 135 can then be generated using new joint dataset 240 by the methodology used to generate the original parameter estimates w 135, which is described above.

EXAMPLE II

An Alternative Logit Model of Hypertension

FIGS. 15-16 provide examples of parameter estimates, probabilities, and updated parameter estimates for an alternative logit model of hypertension, according to an embodiment of the invention illustrated by an Example II. The methodology used in Example II is identical to that described in Example I, with the exception that parameter estimates w 135 and updated parameter estimates w 135 in Example II are generated using machine-readable code for nonlinear least-squares estimation of a logit model. Referring to the generalized method of moments equation in Eq. 12, the values of g(Y, X, w) and W corresponding to nonlinear least-squares estimation of the logit model in Eq. 17 are as follows:

$$g(Y, X, \omega = \{\beta\}) = \frac{1}{N}\sum_{i=1}^{N}[Y_i - \Lambda(X_i'\beta)]\frac{\partial \Lambda(X_i'\beta)}{\partial \beta}, W = I. \quad \text{Eq. 19}$$

EXAMPLE III

A Probit Model of Early-Stage Coronary Artery Disease

FIGS. 17-18 provide examples of parameter estimates, probabilities, and updated parameter estimates for a probit model of early-stage coronary artery disease, according to an embodiment of the invention illustrated by an Example III. The event of interest Y in this probability regression model is formulated as a binomial event:

$$Y = \begin{cases} 0 & \text{if early-stage coronary artery disease is not present} \\ 1 & \text{if early-stage coronary artery disease is present} \end{cases}.$$

The probability regression model specified in Example III is a specific case of the probability regression model in Eq. 14.

Referring to Example III, this embodiment of system 100 performs as follows to generate parameter estimates w 135 (shown in FIG. 17) of the probability regression model specified in that example. The disease status information retrieved from database 300 according to step 213 is variables (2)-(4) of Dataset A, the percentage stenosis in the three major coronary arteries. These variables can be transformed into specifications Y 112 and 122 of a cardiovascular disease event, which is in this example the existence of early-stage coronary artery disease, according to step 214 using the following transformation $$Y = \begin{cases} 0 & \text{if } RCA < 30 \text{ and } LAD < 30 \text{ and } LCX < 30 \\ 1 & \text{if } RCA \geq 30 \text{ and } LAD \geq 30 \text{ and } LCX \geq 30 \end{cases}.$$

These transformed data form dataset 210 of specifications Y 112 and 122 of the existence of early-stage coronary artery disease.

The data derived from cardiovascular sound signals retrieved from database 300 according to step 224 are variables (7)-(9), (10)-(12), and (13)-(15) of Dataset A. These represent the number of beats recorded at each recording location, the Flow Murmur Score generated at each recording location, and the number of S3 sounds recorded at each recording location. According to step 225, the following transformation of these variables can be used to transform them into predictors X 114 and 124 derived from cardiovascular sound signals:

$$AVGS3 = \frac{1}{3}\left(\frac{S3\_R}{BEATS\_R} + \frac{S3\_C}{BEATS\_C} + \frac{S3\_L}{BEATS\_L}\right).$$

These transformed data plus the Flow Murmur Scores form dataset 220 of predictors X 114 and 124 derived from cardiovascular sound signals.

The clinical data retrieved from database 300 according to step 233 are variables (27) and (28) of Dataset A, the height and weight. According to step 234, the following transformation of these variables can be used to transform them into predictors X 116 and 126 based on clinical data:

$$BMI = 703 \times \frac{WEIGHT}{HEIGHT^2}.$$

These transformed data form dataset 230 of predictors X 116 and 126 based on clinical data.

Datasets 210, 220, and 230 are then joined according to step 241. Because this probability regression model applies specifically to those no more than 60 years old, those records corresponding to those of subjects 110 and 120 who are older than 60 years are removed according to step 242; because 17 out of 40 subjects in Dataset A are older than 60 years, this implies that N=23. The result of this last step is joint dataset 240. Joint dataset 240 is then used as input to parameter estimate generator 130 for generation of parameter estimates w 135 using machine-readable code for maximum-likelihood estimation of a probit model.

Again referring to Example III, this embodiment of system 100 performs as follows to generate a probability Pr(Y|X, w) 155 (shown in FIG. 18) of the existence of early-stage coronary artery disease using the probability regression model specified in that example. The data derived from cardiovascular sound signals retrieved from database 300 according to step 424 are variables (7)-(9), (10)-(12), and (13)-(15) of Dataset B. These represent the number of beats recorded at each recording location, the Flow Murmur Score at each recording location, and the number of S3 sounds recorded at each recording location. According to step 425, the following transformation of these variables can be used to transform them into predictors X 144 derived from cardiovascular sound signals:

$$AVGS3 = \frac{1}{3}\left(\frac{S3\_R}{BEATS\_R} + \frac{S3\_C}{BEATS\_C} + \frac{S3\_L}{BEATS\_L}\right).$$

These transformed data plus the Flow Murmur Scores form dataset 420 of predictors X 144 derived from cardiovascular sound signals.

The clinical data retrieved from database 300 according to step 433 are variables (27) and (28) of Dataset A, the height and weight. According to step 434, the following transformation of these variables can be used to transform them into predictors X 146 based on clinical data:

$$BMI = 703 \times \frac{WEIGHT}{HEIGHT^2}.$$

These transformed data form dataset 430 of predictors X 146 based on clinical data.

Datasets 420 and 430 are then joined according to step 441. Because this model applies specifically to those no more than 60 years old, the record is examined according to step 442 to ensure that new subject 140 is no more than 60 years old;

probability Pr(Y|X, w) 155 is not generated for a new subject 140 who is older than 60 years old. The result of this last step is joint dataset 440. Joint dataset 440 and previously generated parameter estimates w 135 are then used as inputs to probability generator 150 for generation of probability Pr(Y|X, w) 155 of the existence of early-stage coronary artery disease using machine-readable code for mathematically evaluating a probit model. The task described in this paragraph is performed for each new subject in Dataset B. Because 9 out of 10 new subjects 140 in Dataset B are no more than 60 years old, probabilities Pr(Y|X, w) 155 are generated for only those 9 subjects.

Again referring to Example III, this embodiment of system 100 performs as follows to update the parameter estimates w 135 (shown in FIG. 18) of the probability regression model specified in that example. This task can be performed because optional disease status information was indeed collected from each of the new subjects 140 in Dataset B. The disease status information for each of the new subjects 140 is variables (2)-(4) of Dataset B, the percentage stenosis in the three major coronary arteries, which is entered into database 300 according to step 212.

The procedure described above for generating a joint dataset 240 can be applied to generate a new joint dataset 240 that contains records of subjects from Dataset B in addition to records of subjects from Dataset A. Because 9 out of 10 new subjects 140 in Dataset B are no more than 60 years old, this implies that N=32 in new joint dataset 240. Updated parameter estimates w 135 can then be generated using new joint dataset 240 by the methodology used to generate the original parameter estimates w 135, which is described above.

EXAMPLE IV

An Ordered Probit Model of Coronary Artery Disease

FIGS. 19-20 provide examples of parameter estimates, probabilities, and updated parameter estimates for an ordered probit model of coronary artery disease, according to an embodiment of the invention illustrated by an Example IV. The event of interest Y in this probability regression model is formulated as an ordered trinomial event:

$$Y = \begin{cases} 0 & \text{if coronary artery disease is not present} \\ 1 & \text{if mild coronary artery disease is present} \\ 2 & \text{if significant coronary artery disease is present} \end{cases}.$$

The probability regression model specified in Example IV is a specific case of the probability regression model in Eq. 14.

Referring to Example IV, this embodiment of system 100 performs as follows to generate parameter estimates w 135 (shown in FIG. 19) of the probability regression model specified in that example. The disease status information retrieved from database 300 according to step 213 is variables (2)-(4) of Dataset A, the percentage stenosis in the three major coronary arteries. These variables can be transformed into specifications Y 112 and 122 of a cardiovascular disease event, which is in this example the existence of a degree of coronary artery disease, according to step 214 using the following transformation:

$$Y = \begin{cases} 0 & \text{if } RCA < 30 \text{ and } LAD < 30 \text{ and } LCX < 30 \\ 1 & \text{if } 30 \leq RCA < 70 \text{ and } 30 \leq LAD < 70 \text{ and } 30 \leq LCX < 70 \\ 2 & \text{if } RCA \geq 70 \text{ and } LAD \geq 70 \text{ and } LCX \geq 70 \end{cases}.$$

These transformed data form dataset 210 of specifications Y 112 and 122 of the existence of a degree of coronary artery disease.

The data derived from cardiovascular sound signals retrieved from database 300 according to step 224 are variables (7)-(9), (10)-(12), and (13)-(15) of Dataset A. These represent the number of beats recorded at each recording location, the Flow Murmur Score generated at each recording location, and the number of S3 sounds recorded at each recording location. According to step 225, the following transformation of these variables can be used to transform them into predictors X 114 and 124 derived from cardiovascular sound signals:

$$AVGS3 = \frac{1}{3}\left(\frac{S3\_R}{BEATS\_R} + \frac{S3\_C}{BEATS\_C} + \frac{S3\_L}{BEATS\_L}\right).$$

These transformed data plus the Flow Murmur Scores form dataset 220 of predictors X 114 and 124 derived from cardiovascular sound signals.

The clinical data retrieved from database 300 according to step 233 are variables (27) and (28) of Dataset A, the height and weight. According to step 234, the following transformation of these variables can be used to transform them into predictors X 116 and 126 based on clinical data:

$$BMI = 703 \times \frac{WEIGHT}{HEIGHT^2}.$$

These transformed data form dataset 230 of predictors X 116 and 126 based on clinical data.

Datasets 210, 220, and 230 are then joined according to step 241. Because this probability regression model applies specifically to those no more than 60 years old, those records corresponding to those of subjects 110 and 120 who are older than 60 years are removed according to step 242; because 17 out of 40 subjects in Dataset A are more than 60 years old, this implies that N=23. The result of this last step is joint dataset 240. Joint dataset 240 is then used as input to parameter estimate generator 130 for generation of parameter estimates w 135 using machine-readable code for maximum-likelihood estimation of an ordered probit model.

Again referring to Example IV, this embodiment of system 100 performs as follows to generate a probability Pr(Y|X, w) 155 (shown in FIG. 20) of the existence of a degree of coronary artery disease using the probability regression model specified in that example. The data derived from cardiovascular sound signals retrieved from database 300 according to step 424 are variables (7)-(9), (10)-(12), and (13)-(15) of Dataset B. These represent the number of beats recorded at each recording location, the Flow Murmur Score generated at each recording location, and the number of S3 sounds recorded at each recording location. According to step 425, the following transformation of these variables can be used to transform them into predictors X 144 derived from cardiovascular sound signals:

$$AVGS3 = \frac{1}{3}\left(\frac{S3\_R}{BEATS\_R} + \frac{S3\_C}{BEATS\_C} + \frac{S3\_L}{BEATS\_L}\right).$$

These transformed data plus the Flow Murmur Scores form dataset 420 of predictors X 144 derived from cardiovascular sound signals.

The clinical data retrieved from database 300 according to step 433 are variables (27) and (28) of Dataset A, the height and weight. According to step 434, the following transformation of these variables can be used to transform them into predictors X 146 based on clinical data:

$$BMI = 703 \times \frac{WEIGHT}{HEIGHT^2}.$$

These transformed data form dataset 430 of predictors X 146 based on clinical data.

Datasets 420 and 430 are then joined according to step 441. Because this probability regression model applies specifically to those no more than 60 years old, the record is examined according to step 442 to ensure that new subject 140 is no more than 60 years old; probability Pr(Y|X, w) 155 is not generated for a new subject 140 that is older than 60 years old. The result of this last step is joint dataset 440. Joint dataset 440 and the previously generated parameter estimates w 135 are then used as inputs to probability generator 150 for generation of probability Pr(Y|X, w) 155 of the existence of a degree of coronary artery disease using machine-readable code for mathematically evaluating an ordered probit model. The task described in this paragraph is performed for each new subject in Dataset B. Because 9 out of 10 new subjects 140 in Dataset B are no more than 60 years old, probabilities Pr(Y|X, w) 155 are generated for only those 9 subjects.

Again referring to Example IV, this embodiment of system 100 performs as follows to update the parameter estimates w 135 (shown in FIG. 20) of the probability regression model specified in that example. This task can be performed because optional disease status information was indeed collected from each of the new subjects 140 in Dataset B. The disease status information for each of the new subjects 140 is variables (2)-(4) of Dataset B, the percentage stenosis in the three major coronary arteries, which is entered into database 300 according to step 212.

The procedure described above for generating a joint dataset 240 can be applied to generate a new joint dataset 240 which contains records of subjects from Dataset B in addition to records of subjects from Dataset A. Because 9 out of 10 new subjects 140 in Dataset B are no more than 60 years old, this implies that N=32 in new joint database 240. Updated parameter estimates w 135 can then be generated using a new joint dataset 240 by the methodology used to generate the original parameter estimates w 135, which is described above.

Additional Points

Probability regression modeling for cardiovascular disease using embodiments of this invention represents an improvement over the prior methods of modeling cardiovascular disease in several ways.

In many ways one or more embodiments of the invention are more convenient than prior approaches. For example, one or more embodiments of the invention use a particular cardiovascular diagnostic mode, cardiovascular sound detection, that is typically non-invasive and hence not risky to a subject being analyzed, which contrasts sharply with the majority of prior cardiovascular diagnostic modes. Additionally, one or more embodiments of the invention advantageously use data that is relatively easily collected from a subject.

Advantageously, one or more embodiments of the invention use high-technology techniques to achieve superior results. For example, a parameter estimate of a probability regression model and the probability of a cardiovascular disease event can often be easily generated using readily available software according to one or more embodiments of the invention. Additionally, one or more embodiments of the invention can be easily implemented over an online network (e.g., the Internet), permitting simultaneous, real-time generation of probabilities or updating of parameter estimates at numerous locations.

One or more embodiments of the invention can produce results more accurately than prior approaches. For example, a probability generated by a probability regression model according to one or more embodiments of the invention is an objective rather than a subjective probability, so its interpretation flows logically from the assumptions used to construct the model rather than from the perception of the one who observes it, allowing a uniformity of interpretation across observers. Additionally, one or more embodiments of the invention can be continuously improved upon by updating one or more parameter estimates as data from additional subjects become available. Moreover, many of the assumptions present in a probability regression model according to one or more embodiments of the invention, e.g., the choice of distribution function F or the choice of predictors X based on cardiovascular sound signals, can be easily altered if additional information about the event of interest Y being modeled becomes available.

One or more embodiments of the invention can also monitor one or more parameters or characteristics in ways that are not readily apparent when using prior approaches. For example, one or more embodiments of the invention capture discriminatory characteristics of a predictor X based on cardiovascular sound signals or a predictor X based on clinical data that are not necessarily obvious when using the predictor itself to diagnose cardiovascular disease, e.g., the presence of nonlinearity or nonmonotonicity in the predictor. Additionally, one or more embodiments of the invention capture interactions between two or more predictors that are not readily apparent when using these predictors independently. Moreover, the size of the dataset needed to obtain substantially accurate values of one or more parameter estimates according to one or more embodiments of the invention is typically much smaller in practice than other methods relying on statistical sampling, such as neural networks.

Additional advantages other than the aforementioned advantages also exist, as will be appreciated by those skilled in the art.

From the foregoing, it can be seen that a method and system for modeling cardiovascular disease using a probability regression model is provided. Specific embodiments have been described above in connection with multiple general applications that are capable of determining one or more parameters of a probability regression model and/or generating a probability based on the probability regression model. Additionally, specific embodiments have been described in the context of specific applications and examples of system configurations and operational variations.

It will be appreciated, however, that embodiments of the invention can be in other specific forms without departing from the spirit or essential characteristics thereof. For example, while some embodiments have been described in the context of general applications, specific applications, and multiple examples, it will be appreciated that aspects of each of these can be intermixed as desired to achieve the desired system performance. Additionally, elements can be added to or omitted from the examples discussed above as desired to obtain desirable results. The presently disclosed embodiments are considered in all respects to be illustrative and not restrictive.

What is claimed is:

1. A processor-readable medium comprising code representing instructions to cause a processor to:
    generate at least one parameter estimate of a probability regression model for cardiovascular disease at least partially based on (1) a plurality of predictors generated from cardiovascular sound signals of a plurality of subjects and (2) disease status information for cardiovascular disease of the plurality of subjects;
    determine a probability of cardiovascular disease for a new subject with the probability regression model, the probability of cardiovascular disease being generated at least partially based on the at least one parameter estimate and another plurality of predictors generated from cardiovascular sound signals of the new subject; and
    update the at least one parameter estimate at least partially based on disease status information associated with the new subject.

2. The processor-readable medium of claim 1, further comprising code representing instructions to cause a processor to:
    determine a probability of cardiovascular disease for a second new subject with the probability regression model, the probability of cardiovascular disease for the second new subject being generated at least partially based on the updated at least one parameter estimate.

3. A processor-readable medium comprising code representing instructions to cause a processor to:
    generate a probability of cardiovascular disease using a probability regression model:

$$Pr(Y \mid X, b) = \frac{1}{\sqrt{2\pi}} \int_{s=-\infty}^{X'b} \exp\left(-\frac{s^2}{2}\right) ds;$$

wherein X is at least one predictor generated from cardiovascular sound signals;
    wherein b is at least one parameter estimate previously generated from the probability regression model based on cardiovascular sound signals of a plurality of subjects; and
    wherein Pr(Y|X, b) is the probability of the existence of cardiovascular disease Y given the at least one predictor X and the at least one previously generated parameter estimate b.

4. The processor-readable medium of claim 3, wherein the at least one previously generated parameter estimate b is previously generated from the probability regression model also based on clinical data of the plurality of subjects.

5. A processor-readable medium comprising code representing instructions to cause a processor to:
    generate at least one parameter estimate of a probability regression model for cardiovascular disease at least partially based on (1) a predictor generated from cardiovascular sound signals of at least one subject and (2) disease status information for cardiovascular disease;
    wherein the probability regression model is one of a logit model, a multinomial probit model, a multinomial logit model, an ordered probit model, an ordered logit model, a Weibull model, a Cox proportional hazards model, an exponential model, a log-logistic model, a lognormal model, and a Kaplan-Meier model.

6. The processor-readable medium of claim 5, further comprising code representing instructions to cause a processor to:
    update the at least one parameter estimate at least partially based on information associated with a new subject.

7. The processor-readable medium of claim 5, wherein the cardiovascular disease is coronary artery disease.

8. The processor-readable medium of claim 5, wherein the cardiovascular disease is one of carotid artery disease, congestive heart failure, hypertension, and bundle branch block.

9. The processor-readable medium of claim 5, wherein the probability regression model is a model of a current cardiovascular disease event.

10. The processor-readable medium of claim 5, wherein the probability regression model is a model of a future cardiovascular disease event.

11. The processor-readable medium of claim 5, wherein the predictor is indicative of bruits present in the cardiovascular sound signals of the at least one subject.

12. The processor-readable medium of claim 5, wherein the predictor is indicative of a third heart sound present in the cardiovascular sound signals of the at least one subject.

13. The processor-readable medium of claim 5, wherein the predictor is indicative of a fourth heart sound present in the cardiovascular sound signals of the at least one subject.

14. The processor-readable medium of claim 5, wherein the predictor is indicative of peak acoustic power present in a diastolic interval of the cardiovascular sound signals of the at least one subject.

15. The processor-readable medium of claim 5, wherein the predictor is one of a plurality of predictors, each predictor from the plurality of predictors being generated from the cardiovascular sound signals of the at least one subject.

16. The processor-readable medium of claim 15, the plurality of predictors being different ones of:
    a predictor indicative of bruits present in the cardiovascular sound signals of the at least one subject;
    a predictor indicative of a third heart sound present in the cardiovascular sound signals of the at least one subject;
    a predictor indicative of a fourth heart sound present in the cardiovascular sound signals of the at least one subject; and
    a predictor indicative of peak acoustic power present in a diastolic interval of the cardiovascular sound signals of the at least one subject.

17. The processor-readable medium of claim 5, wherein the generating of the at least one parameter estimate also uses at least one supplemental predictor that is not generated from the cardiovascular sound signals of the at least one subject.

18. The processor-readable medium of claim 17, wherein the at least one supplemental predictor includes a heart rate of the at least one subject.

19. The processor-readable medium of claim 17, wherein the at least one supplemental predictor includes at least one of:
    a sex of the at least one subject;
    an age of the at least one subject;
    a body mass index of the at least one subject;
    a cholesterol level of the at least one subject;
    a C-reactive protein level of the at least one subject; and
    a socioeconomic classification of the at least one subject.

20. The processor-readable medium of claim 17, wherein the at least one supplemental predictor includes at least one of:
sex, age, diabetic state, cholesterol level, C-reactive protein level, chest morphology data, chest hair data, breast size data, body mass index, and blood viscosity data.

21. The processor-readable medium of claim 5, wherein the disease status information for cardiovascular disease includes a categorical indication of a degree of cardiovascular disease.

22. The processor-readable medium of claim 5, wherein the disease status information for cardiovascular disease includes at least one of:
information from a catheterization analysis;
information from an electrocardiogram analysis;
information from a stress-test analysis;
information from an echocardiographic analysis;
information from an electron-beam tomography analysis; and
information from a magnetic resonance imaging analysis.

23. The processor-readable medium of claim 5, wherein the parameter estimate is generated by a method of maximum likelihood.

24. The processor-readable medium of claim 5, wherein the parameter estimate is generated by one of a generalized method of moments, a simulation method, and an exact method.

25. The processor-readable medium of claim 5, wherein the at least one generated parameter estimate is one of a plurality of generated parameter estimates of a probability regression model for cardiovascular disease.

26. The processor-readable medium of claim 25, wherein the predictor is one of a plurality of predictors generated from cardiovascular sound signals of the at least one subject.

27. The processor-readable medium of claim 25, wherein the predictor is one of a plurality of predictors generated from cardiovascular sound signals of a plurality of different subjects.

28. The processor-readable medium of claim 27, wherein the plurality of different subjects include at least a first group of subjects and a second group of subjects, the first group of subjects having a common first characteristic and the second group of subjects having a common second characteristic, the first characteristic being different from the second characteristic.

29. The processor-readable medium of claim 28, the first characteristic and the second characteristic being different ones of:
sex, age, diabetic status, and smoking status.

30. The processor-readable medium of claim 5, wherein the at least one subject is a plurality of subjects.

31. The processor-readable medium of claim 5, the at least one subject being a plurality of subjects, the at least one parameter estimate being a first parameter estimate for the plurality of subjects, the processor-readable medium further comprising code representing instructions to cause a processor to update the method of modeling cardiovascular disease by:
generating a second parameter estimate of the probability regression model for cardiovascular disease using (1) a new set of predictors generated from cardiovascular sound signals of a new set of subjects and (2) clinical data of the new set of subjects, the clinical data including disease status information for cardiovascular disease.

32. A processor-readable medium comprising code for predicting cardiovascular disease, the code representing instructions to cause a processor to:
generate a probability of cardiovascular disease using a probability regression model, the probability regression model using at least one predictor generated from cardiovascular sound signals;
wherein the probability regression model is one of a logit model, a multinomial probit model, a multinomial logit model, an ordered probit model, an ordered logit model, a Weibull model, a Cox proportional hazards model, an exponential model, a log-logistic model, a lognormal model, and a Kaplan-Mejer model.

33. The processor-readable medium of claim 32, wherein the cardiovascular disease is coronary artery disease.

34. The processor-readable medium of claim 32, wherein the cardiovascular disease is one of carotid artery disease, congestive heart failure, hypertension, and bundle branch block.

35. The processor-readable medium of claim 32, wherein the probability regression model is a model of a current cardiovascular disease event.

36. The processor-readable medium of claim 32, wherein the probability regression model is a model of a future cardiovascular disease event.

37. The processor-readable medium of claim 32, wherein the at least one predictor is indicative of bruits present in the cardiovascular sound signals.

38. The processor-readable medium of claim 32, wherein the at least one Predictor is indicative of a third heart sound present in the cardiovascular sound signals.

39. The processor-readable medium of claim 32, wherein the at least one predictor is indicative of a fourth heart sound present in the cardiovascular sound signals.

40. The processor-readable medium method of claim 32, wherein the at least one predictor is indicative of peak acoustic power present in a diastolic interval of the cardiovascular sound signals.

41. The processor-readable medium of claim 32, wherein the at least one predictor includes a plurality of predictors each generated from the cardiovascular sound signals.

42. The processor-readable medium of claim 41, the plurality of predictors being different ones of:
a predictor indicative of bruits present in the cardiovascular sound signals;
a predictor indicative of a third heart sound present in the cardiovascular sound signals;
a predictor indicative of a fourth heart sound present in the cardiovascular sound signals; and
a predictor indicative of peak acoustic power present in a diastolic interval of the cardiovascular sound signals.

43. The processor-readable medium of claim 32, wherein the code representing instructions to cause a processor to generate the probability of cardiovascular disease also uses at least one supplemental predictor that is not generated from the cardiovascular sound signals.

44. The processor-readable medium of claim 43, wherein the at least one supplemental predictor that is not generated from the cardiovascular sound signals includes a heart rate.

45. The processor-readable medium of claim 43, wherein the at least one supplemental predictor that is not generated from the cardiovascular sound signals includes at least one of a sex, an age, a body mass index, a cholesterol level, a C-reactive protein level, and a socioeconomic indicator.

46. The processor-readable medium of claim 32, wherein the at least one supplemental predictor is also generated from clinical data.

47. The processor-readable medium of claim 46, wherein the clinical data includes at least one of sex, age, diabetic state, cholesterol level, C-reactive protein level, chest morphology data, chest hair data, breast size data, body mass index, and blood viscosity data.

48. The processor-readable medium of claim 32, wherein the probability regression model includes at least one previously generated parameter estimate.

49. The processor-readable medium of claim 48, wherein the cardiovascular sound signals are first cardiovascular sound signals, the parameter estimate being generated using at least another predictor that is generated from second cardiovascular sound signals that are different than the first cardiovascular sound signals.

50. The processor-readable medium of claim 46, wherein the parameter estimate is also generated using clinical data that at least includes disease status information for cardiovascular disease.

51. A system comprising:
   a processor configured to use a probability regression model for cardiovascular disease; and
   a parameter estimate generator configured to generate a parameter estimate for the probability regression model using (1) a predictor generated from cardiovascular sound signals of at least one subject and (2) disease status information for cardiovascular disease;
   wherein the probability regression model is one of a logit model, a multinomial probit model, a multinomial logit model, an ordered probit model, an ordered logit model, a Weibull model, a Cox proportional hazards model, an exponential model, a log-logistic model, a lognormal model, and a Kaplan-Meier model.

52. The system of claim 51, wherein the processor is further configured to determine a probability of cardiovascular disease using the probability regression model and the parameter estimate.

53. A system comprising:
   a memory configured to store a probability regression model for cardiovascular disease; and
   a probability generator configured to generate a probability of cardiovascular disease using the probability regression model, the probability regression model using at least one predictor generated from cardiovascular sound signals;
   wherein the probability regression model is one of a logit model, a multinomial probit model, a multinomial logit model, an ordered probit model, an ordered logit model, a Weibull model, a Cox proportional hazards model, an exponential model, a log-logistic model, a lognormal model, and a Kaplan-Meier model.

* * * * *

UNITED STATES PATENT AND TRADEMARK OFFICE
CERTIFICATE OF CORRECTION

| | | |
|---|---|---|
| PATENT NO. | : 7,462,153 B2 | Page 1 of 1 |
| APPLICATION NO. | : 10/897121 | |
| DATED | : December 9, 2008 | |
| INVENTOR(S) | : Bostian et al. | |

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 659 days Delete the phrase "by 659 days" and insert -- by 1082 days --

Signed and Sealed this

Twenty-fourth Day of August, 2010

David J. Kappos
*Director of the United States Patent and Trademark Office*